(12) United States Patent
Whitman et al.

(10) Patent No.: US 9,113,847 B2
(45) Date of Patent: *Aug. 25, 2015

(54) ELECTRO-MECHANICAL SURGICAL DEVICE

(71) Applicant: COVIDIEN LP, Mansfield, MA (US)

(72) Inventors: Michael P. Whitman, New Hope, PA (US); John E. Burbank, Ridgefield, CT (US); David A. Zeichner, Oxford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/737,084

(22) Filed: Jan. 9, 2013

(65) Prior Publication Data

US 2013/0131650 A1 May 23, 2013

Related U.S. Application Data

(60) Continuation of application No. 11/049,631, filed on Feb. 1, 2005, now Pat. No. 8,357,144, which is a continuation of application No. 10/256,681, filed on Sep. 26, 2002, now Pat. No. 6,849,071, which is a (Continued)

(51) Int. Cl.
*A61B 17/00* (2006.01)
*A61B 10/02* (2006.01)

(Continued)

(52) U.S. Cl.
CPC ............. *A61B 17/00* (2013.01); *A61B 10/0233* (2013.01); *A61B 17/072* (2013.01); *A61B 17/07207* (2013.01); *A61B 17/115* (2013.01); *A61B 17/1114* (2013.01); *A61B 17/00491* (2013.01); *A61B 17/11* (2013.01);

(Continued)

(58) Field of Classification Search
USPC ................................ 606/1, 130; 600/102, 104
See application file for complete search history.

(56) References Cited

U.S. PATENT DOCUMENTS

| 1,831,250 A | 10/1932 | Tomlinson |
| 3,079,606 A | 3/1963 | Bobrov et al. |

(Continued)

FOREIGN PATENT DOCUMENTS

| DE | 2903159 | 7/1980 |
| DE | 3300768 | 7/1984 |

(Continued)

OTHER PUBLICATIONS

Gardner, The Best Doctors in New York, New York Magazine, Jun. 10, 2002, p. 80 (1 p.).

*Primary Examiner* — Ahmed Farah
*Assistant Examiner* — Jeffrey Lipitz

(57) ABSTRACT

An electromechanical surgical device includes a motor system configured to drive drive-shafts and a steering cable arrangement. A control system may be provided for controlling the motor system. A remote control unit may also be provided for controlling the motor system via the control system. Optical or Hall-effect devices, may be provided for determining the position of the elements of the surgical instrument based on the detected rotation of the drive-shafts. A memory unit stores a plurality of operating programs or algorithms, each corresponding to a type of surgical instrument attachable to the electro-mechanical surgical device. The control system reads or selects from the plurality of operating programs or algorithms, the operating program or algorithm corresponding to the type of surgical instrument attached to the electromechanical surgical device.

16 Claims, 20 Drawing Sheets

Related U.S. Application Data division of application No. 09/723,715, filed on Nov. 28, 2000, now Pat. No. 6,793,652, which is a continuation-in-part of application No. 09/324,451, filed on Jun. 2, 1999, now Pat. No. 6,315,184, and a continuation-in-part of application No. 09/324,452, filed on Jun. 2, 1999, now Pat. No. 6,443,973, and a continuation-in-part of application No. 09/351,534, filed on Jul. 12, 1999, now Pat. No. 6,264,087, and a continuation-in-part of application No. 09/510,923, filed on Feb. 22, 2000, now Pat. No. 6,517,565, and a continuation-in-part of application No. 09/510,927, filed on Feb. 22, 2000, now Pat. No. 6,716,233, and a continuation-in-part of application No. 09/510,932, filed on Feb. 22, 2000, now Pat. No. 6,491,201, said application No. 09/510,923 is a continuation-in-part of application No. 09/324,452, filed on Jun. 2, 1999, now Pat. No. 6,443,973, said application No. 09/510,927 is a continuation-in-part of application No. 09/324,452, filed on Jun. 2, 1999, now Pat. No. 6,443,973.

(51) Int. Cl.
*A61B 17/072* (2006.01)
*A61B 17/115* (2006.01)
*A61B 17/11* (2006.01)
*A61B 19/00* (2006.01)
*A61B 17/29* (2006.01)
*A61B 17/32* (2006.01)
*A61B 17/3211* (2006.01)

(52) U.S. Cl.
CPC .... *A61B 19/2203* (2013.01); *A61B 2010/0208* (2013.01); *A61B 2017/003* (2013.01); *A61B 2017/00022* (2013.01); *A61B 2017/00039* (2013.01); *A61B 2017/00199* (2013.01); *A61B 2017/00323* (2013.01); *A61B 2017/00398* (2013.01); *A61B 2017/00464* (2013.01); *A61B 2017/00473* (2013.01); *A61B 2017/00482* (2013.01); *A61B 2017/00734* (2013.01); *A61B 2017/0725* (2013.01); *A61B 2017/07214* (2013.01); *A61B 2017/07271* (2013.01); *A61B 2017/2905* (2013.01); *A61B 2017/2943* (2013.01); *A61B 2017/320052* (2013.01); *A61B 2017/32113* (2013.01); *A61B 2019/2242* (2013.01)

(56) References Cited

U.S. PATENT DOCUMENTS

| | | |
|---|---|---|
| 3,193,165 A | 7/1965 | Akhalaya et al. |
| 3,256,875 A | 6/1966 | Tsepelev et al. |
| 3,388,847 A | 6/1968 | Kasulin et al. |
| 3,490,675 A | 1/1970 | Green et al. |
| 3,494,533 A | 2/1970 | Green et al. |
| 3,552,626 A | 1/1971 | Astafiev et al. |
| 3,568,659 A | 3/1971 | Karnegis |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 3,952,748 A | 4/1976 | Kaliher et al. |
| 4,027,510 A | 6/1977 | Hiltebrandt |
| 4,071,029 A | 1/1978 | Richmond et al. |
| 4,085,756 A | 4/1978 | Weaver |
| 4,198,960 A | 4/1980 | Utsugi |
| 4,198,982 A | 4/1980 | Fortner et al. |
| 4,202,479 A | 5/1980 | Razgulov et al. |
| 4,207,898 A | 6/1980 | Becht |
| 4,250,873 A | 2/1981 | Bonnet |
| 4,273,109 A | 6/1981 | Enderby |
| 4,273,111 A | 6/1981 | Tsukaya |
| 4,282,884 A | 8/1981 | Boebel |
| 4,286,585 A | 9/1981 | Ogawa |
| 4,289,131 A | 9/1981 | Mueller |
| 4,289,133 A | 9/1981 | Rothfuss |
| 4,304,236 A | 12/1981 | Conta et al. |
| 4,305,126 A | 12/1981 | Beier et al. |
| 4,310,115 A | 1/1982 | Inoue |
| 4,319,576 A | 3/1982 | Rothfuss |
| 4,334,539 A | 6/1982 | Childs et al. |
| 4,351,466 A | 9/1982 | Noiles |
| 4,367,729 A | 1/1983 | Ogiu |
| 4,379,457 A | 4/1983 | Gravener et al. |
| 4,402,311 A | 9/1983 | Hattori |
| 4,423,730 A | 1/1984 | Gabbay |
| 4,429,695 A | 2/1984 | Green |
| 4,440,170 A | 4/1984 | Golden et al. |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,520,817 A | 6/1985 | Green |
| 4,534,420 A | 8/1985 | Goldelius |
| 4,535,773 A | 8/1985 | Yoon |
| 4,559,928 A | 12/1985 | Takayama |
| 4,573,468 A | 3/1986 | Conta et al. |
| 4,574,806 A | 3/1986 | McCarthy |
| 4,576,167 A | 3/1986 | Noiles |
| 4,589,412 A | 5/1986 | Kensey |
| 4,589,582 A | 5/1986 | Bilotti |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,610,383 A | 9/1986 | Rothfuss et al. |
| D286,567 S | 11/1986 | Lichtman et al. |
| 4,631,052 A | 12/1986 | Kensey |
| 4,633,861 A | 1/1987 | Chow et al. |
| 4,633,874 A | 1/1987 | Chow et al. |
| 4,644,952 A | 2/1987 | Patipa et al. |
| 4,646,745 A | 3/1987 | Noiles |
| 4,655,673 A | 4/1987 | Hawkes |
| 4,667,673 A | 5/1987 | Li |
| 4,671,445 A | 6/1987 | Barker et al. |
| 4,672,961 A | 6/1987 | Davies |
| 4,674,515 A | 6/1987 | Andou et al. |
| 4,682,596 A | 7/1987 | Bales et al. |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,729,763 A | 3/1988 | Henrie |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |

(56) References Cited

U.S. PATENT DOCUMENTS

| | | |
|---|---|---|
| 4,805,823 A | 2/1989 | Rothfuss |
| 4,813,928 A | 3/1989 | Abe et al. |
| 4,815,469 A | 3/1989 | Cohen et al. |
| 4,817,847 A | 4/1989 | Redtenbacher et al. |
| 4,819,632 A | 4/1989 | Davies |
| 4,855,819 A | 8/1989 | Hibino et al. |
| 4,867,158 A | 9/1989 | Sugg |
| 4,869,415 A | 9/1989 | Fox |
| 4,873,977 A | 10/1989 | Avant et al. |
| 4,887,599 A | 12/1989 | Muller |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,907,973 A | 3/1990 | Hon |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,941,454 A | 7/1990 | Wood et al. |
| 4,943,277 A | 7/1990 | Bolling |
| 4,955,882 A | 9/1990 | Hakky |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,978,049 A | 12/1990 | Green |
| 4,982,726 A | 1/1991 | Taira |
| 4,994,060 A | 2/1991 | Rink et al. |
| 4,995,877 A | 2/1991 | Ams et al. |
| 5,005,749 A | 4/1991 | Aranyi |
| 5,037,379 A | 8/1991 | Clayman et al. |
| 5,040,715 A | 8/1991 | Green et al. |
| 5,059,203 A | 10/1991 | Husted |
| 5,065,929 A | 11/1991 | Schulze et al. |
| D322,143 S | 12/1991 | Spreckelmeier |
| 5,071,430 A | 12/1991 | de Salis et al. |
| 5,077,506 A | 12/1991 | Krause |
| 5,084,045 A | 1/1992 | Helenowski |
| 5,104,025 A | 4/1992 | Main et al. |
| 5,129,570 A | 7/1992 | Schulze et al. |
| 5,133,359 A | 7/1992 | Kedem |
| 5,133,360 A | 7/1992 | Spears |
| 5,133,713 A | 7/1992 | Huang et al. |
| 5,133,729 A | 7/1992 | Sjostrom |
| 5,139,513 A | 8/1992 | Segato |
| 5,143,082 A | 9/1992 | Kindberg et al. |
| 5,159,446 A | 10/1992 | Hibino et al. |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,176,687 A | 1/1993 | Hasson et al. |
| 5,184,601 A * | 2/1993 | Putman ........................ 600/102 |
| 5,186,714 A | 2/1993 | Boudreault et al. |
| 5,190,542 A | 3/1993 | Nakao et al. |
| 5,192,292 A | 3/1993 | Cezana et al. |
| 5,197,649 A | 3/1993 | Bessler et al. |
| 5,197,968 A | 3/1993 | Clement |
| 5,201,325 A | 4/1993 | McEwen et al. |
| 5,201,750 A | 4/1993 | Höcherl et al. |
| 5,205,459 A | 4/1993 | Brinkerhoff et al. |
| 5,207,684 A | 5/1993 | Nobles |
| 5,207,691 A | 5/1993 | Nardella |
| 5,207,697 A | 5/1993 | Carusillo et al. |
| 5,215,521 A | 6/1993 | Cochran et al. |
| 5,217,003 A | 6/1993 | Wilk |
| 5,217,030 A | 6/1993 | Yoon |
| 5,221,279 A | 6/1993 | Cook et al. |
| 5,224,951 A | 7/1993 | Freitas |
| 5,226,426 A | 7/1993 | Yoon |
| 5,234,439 A | 8/1993 | Wilk et al. |
| 5,237,884 A | 8/1993 | Seto |
| 5,249,583 A | 10/1993 | Mallaby |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,292,053 A | 3/1994 | Bilotti et al. |
| 5,307,976 A | 5/1994 | Olson et al. |
| 5,312,023 A | 5/1994 | Green et al. |
| 5,312,416 A | 5/1994 | Spaeth et al. |
| 5,318,221 A | 6/1994 | Green et al. |
| 5,326,013 A | 7/1994 | Green et al. |
| 5,330,483 A | 7/1994 | Heaven et al. |
| 5,330,486 A | 7/1994 | Wilk |
| 5,333,773 A | 8/1994 | Main et al. |
| 5,336,237 A | 8/1994 | Chin et al. |
| 5,342,299 A | 8/1994 | Snoke et al. |
| 5,342,382 A | 8/1994 | Brinkerhoff et al. |
| 5,344,420 A | 9/1994 | Hilal et al. |
| 5,346,497 A | 9/1994 | Simon et al. |
| 5,350,104 A | 9/1994 | Main et al. |
| 5,354,266 A | 10/1994 | Snoke |
| 5,354,303 A | 10/1994 | Spaeth et al. |
| 5,358,496 A | 10/1994 | Ortiz et al. |
| 5,358,506 A | 10/1994 | Green et al. |
| 5,364,001 A | 11/1994 | Bryan |
| 5,368,015 A * | 11/1994 | Wilk ........................ 600/104 |
| 5,368,607 A | 11/1994 | Freitas |
| 5,380,321 A | 1/1995 | Yoon |
| 5,383,880 A | 1/1995 | Hooven |
| 5,387,196 A | 2/1995 | Green et al. |
| 5,391,156 A | 2/1995 | Hildwein et al. |
| 5,395,030 A | 3/1995 | Kuramoto et al. |
| 5,395,033 A * | 3/1995 | Byrne et al. ................ 227/175.1 |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,409,487 A | 4/1995 | Jalbert et al. |
| 5,411,508 A | 5/1995 | Bessler et al. |
| 5,413,267 A | 5/1995 | Solyntjes |
| 5,413,268 A | 5/1995 | Green et al. |
| 5,415,334 A | 5/1995 | Williamson et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,454,825 A | 10/1995 | Van Leeuwen et al. |
| 5,460,182 A | 10/1995 | Goodman et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,529,235 A | 6/1996 | Boiarski et al. |

(56) References Cited

U.S. PATENT DOCUMENTS

| | | | |
|---|---|---|---|
| 5,531,687 A | 7/1996 | Snoke et al. | |
| 5,533,661 A | 7/1996 | Main et al. | |
| 5,549,565 A | 8/1996 | Ryan et al. | |
| 5,553,765 A | 9/1996 | Knodel et al. | |
| 5,554,169 A | 9/1996 | Green et al. | |
| RE35,352 E | 10/1996 | Peters | |
| 5,562,677 A | 10/1996 | Hildwein et al. | |
| 5,562,702 A | 10/1996 | Huitema et al. | |
| 5,571,116 A | 11/1996 | Bolanos et al. | |
| 5,582,611 A | 12/1996 | Tsuruta et al. | |
| 5,584,425 A | 12/1996 | Savage et al. | |
| 5,584,848 A | 12/1996 | Yoon | |
| 5,588,579 A | 12/1996 | Schnut et al. | |
| 5,591,186 A | 1/1997 | Wurster et al. | |
| 5,597,107 A | 1/1997 | Knodel et al. | |
| 5,599,347 A | 2/1997 | Hart et al. | |
| 5,609,285 A | 3/1997 | Grant et al. | |
| 5,609,560 A | 3/1997 | Ichikawa et al. | |
| 5,617,857 A | 4/1997 | Chadir et al. | |
| 5,639,008 A | 6/1997 | Gallagher et al. | |
| 5,651,780 A | 7/1997 | Jackson et al. | |
| 5,653,374 A | 8/1997 | Young et al. | |
| 5,653,692 A | 8/1997 | Masterson et al. | |
| 5,662,673 A | 9/1997 | Kieturakis | |
| 5,665,100 A | 9/1997 | Yoon | |
| 5,667,517 A | 9/1997 | Hooven | |
| 5,676,674 A | 10/1997 | Bolanos et al. | |
| 5,693,031 A | 12/1997 | Ryan et al. | |
| 5,709,335 A | 1/1998 | Heck | |
| 5,713,870 A | 2/1998 | Yoon | |
| 5,732,872 A | 3/1998 | Bolduc et al. | |
| 5,735,289 A | 4/1998 | Pfeffer et al. | |
| 5,735,861 A | 4/1998 | Peifer et al. | |
| 5,749,885 A | 5/1998 | Sjostrom et al. | |
| 5,749,893 A | 5/1998 | Vidal et al. | |
| 5,758,814 A | 6/1998 | Gallagher et al. | |
| 5,762,458 A | 6/1998 | Wang et al. | |
| 5,779,130 A | 7/1998 | Alesi et al. | |
| 5,782,396 A | 7/1998 | Mastri et al. | |
| 5,782,397 A | 7/1998 | Koukline | |
| 5,792,135 A | 8/1998 | Madhani et al. | |
| 5,797,835 A | 8/1998 | Green | |
| 5,797,900 A | 8/1998 | Madhani et al. | |
| 5,797,944 A | 8/1998 | Nobles et al. | |
| 5,807,318 A | 9/1998 | St. Goar et al. | |
| 5,807,377 A | 9/1998 | Madhani et al. | |
| 5,814,044 A | 9/1998 | Hooven | |
| 5,815,640 A | 9/1998 | Wang et al. | |
| 5,817,113 A | 10/1998 | Gifford, III et al. | |
| 5,830,191 A | 11/1998 | Hildwein et al. | |
| 5,836,503 A | 11/1998 | Ehrenfels et al. | |
| 5,846,221 A | 12/1998 | Snoke et al. | |
| 5,849,023 A * | 12/1998 | Mericle | 606/180 |
| 5,855,583 A | 1/1999 | Wang et al. | |
| 5,857,996 A | 1/1999 | Snoke | |
| 5,860,953 A | 1/1999 | Snoke et al. | |
| 5,863,366 A | 1/1999 | Snow | |
| 5,868,760 A | 2/1999 | McGuckin, Jr. | |
| 5,868,779 A | 2/1999 | Ruiz | |
| 5,871,471 A | 2/1999 | Ryan et al. | |
| 5,878,193 A | 3/1999 | Wang et al. | |
| 5,881,943 A | 3/1999 | Heck et al. | |
| 5,897,562 A | 4/1999 | Bolanos et al. | |
| 5,907,664 A | 5/1999 | Wang et al. | |
| 5,915,616 A | 6/1999 | Viola et al. | |
| 5,925,055 A | 7/1999 | Adrian et al. | |
| 5,928,261 A | 7/1999 | Ruiz | |
| 5,931,848 A | 8/1999 | Saadat | |
| 5,947,363 A | 9/1999 | Bolduc et al. | |
| 5,951,549 A | 9/1999 | Richardson et al. | |
| 5,954,259 A | 9/1999 | Viola et al. | |
| 5,957,363 A | 9/1999 | Heck | |
| 5,957,882 A | 9/1999 | Nita et al. | |
| 5,957,884 A | 9/1999 | Hooven | |
| 5,976,122 A * | 11/1999 | Madhani et al. | 606/1 |
| 5,976,159 A | 11/1999 | Bolduc et al. | |
| 5,984,919 A | 11/1999 | Hilal et al. | |
| 5,989,274 A | 11/1999 | Davison et al. | |
| 5,993,378 A | 11/1999 | Lemelson | |
| 5,993,454 A | 11/1999 | Longo | |
| 5,997,510 A | 12/1999 | Schwemberger | |
| 6,001,108 A | 12/1999 | Wang et al. | |
| 6,004,335 A | 12/1999 | Vaitekunas et al. | |
| 6,007,512 A | 12/1999 | Hooven | |
| 6,007,531 A | 12/1999 | Snoke et al. | |
| 6,010,493 A | 1/2000 | Snoke | |
| 6,017,322 A | 1/2000 | Snoke et al. | |
| 6,017,354 A * | 1/2000 | Culp et al. | 606/170 |
| 6,059,719 A | 5/2000 | Yamamoto et al. | |
| 6,063,095 A | 5/2000 | Wang et al. | |
| 6,068,627 A | 5/2000 | Orszulak et al. | |
| 6,074,402 A | 6/2000 | Peifer et al. | |
| 6,083,163 A | 7/2000 | Karron et al. | |
| 6,086,600 A | 7/2000 | Kortenbach | |
| 6,090,120 A | 7/2000 | Wright et al. | |
| 6,099,466 A | 8/2000 | Sano et al. | |
| 6,106,512 A | 8/2000 | Eberhardt et al. | |
| 6,119,913 A | 9/2000 | Adams et al. | |
| 6,126,058 A | 10/2000 | Adams et al. | |
| 6,126,591 A | 10/2000 | McGarry et al. | |
| 6,126,651 A | 10/2000 | Mayer | |
| 6,132,368 A | 10/2000 | Cooper | |
| 6,159,196 A | 12/2000 | Ruiz | |
| 6,171,282 B1 | 1/2001 | Ragsdale | |
| 6,174,324 B1 | 1/2001 | Egan et al. | |
| 6,179,837 B1 | 1/2001 | Hooven | |
| D438,617 S | 3/2001 | Cooper et al. | |
| 6,201,984 B1 | 3/2001 | Funda et al. | |
| 6,206,903 B1 | 3/2001 | Ramans | |
| D441,076 S | 4/2001 | Cooper et al. | |
| D441,862 S | 5/2001 | Cooper et al. | |
| 6,237,605 B1 | 5/2001 | Vaska et al. | |
| 6,244,809 B1 | 6/2001 | Wang et al. | |
| 6,246,200 B1 | 6/2001 | Blumenkranz et al. | |
| 6,251,093 B1 | 6/2001 | Valley et al. | |
| D444,555 S | 7/2001 | Cooper et al. | |
| 6,261,273 B1 | 7/2001 | Ruiz | |
| 6,264,087 B1 | 7/2001 | Whitman | |
| 6,280,415 B1 | 8/2001 | Johnson | |
| 6,309,397 B1 | 10/2001 | Julian et al. | |
| 6,312,435 B1 | 11/2001 | Wallace et al. | |
| 6,315,184 B1 | 11/2001 | Whitman | |
| 6,331,181 B1 * | 12/2001 | Tierney et al. | 606/130 |
| 6,346,072 B1 | 2/2002 | Cooper | |
| 6,348,061 B1 | 2/2002 | Whitman | |
| 6,364,888 B1 | 4/2002 | Niemeyer et al. | |
| 6,371,952 B1 | 4/2002 | Madhani et al. | |
| 6,394,998 B1 | 5/2002 | Wallace et al. | |
| 6,398,726 B1 | 6/2002 | Ramans et al. | |
| 6,434,507 B1 | 8/2002 | Clayton et al. | |
| 6,443,973 B1 | 9/2002 | Whitman | |
| 6,488,197 B1 | 12/2002 | Whitman | |
| 6,491,201 B1 | 12/2002 | Whitman | |
| 6,491,701 B2 | 12/2002 | Tierney et al. | |
| 6,517,565 B1 | 2/2003 | Whitman et al. | |
| 6,533,157 B1 | 3/2003 | Whitman | |
| 6,598,912 B2 | 7/2003 | Hillgaertner et al. | |
| 6,651,672 B2 | 11/2003 | Roth | |
| 6,716,233 B1 | 4/2004 | Whitman | |
| 6,719,755 B2 | 4/2004 | Sliwa et al. | |
| 6,764,445 B2 | 7/2004 | Ramans et al. | |
| 6,766,204 B2 | 7/2004 | Niemeyer et al. | |
| 6,866,650 B2 | 3/2005 | Stevens et al. | |
| 6,866,671 B2 | 3/2005 | Tierney et al. | |
| 6,913,600 B2 | 7/2005 | Valley et al. | |
| 6,913,601 B2 | 7/2005 | St. Goar et al. | |
| 6,981,941 B2 | 1/2006 | Whitman et al. | |
| 7,028,692 B2 | 4/2006 | Sterman et al. | |
| 7,048,745 B2 | 5/2006 | Tierney et al. | |
| 7,252,660 B2 | 8/2007 | Kunz | |
| 7,371,210 B2 | 5/2008 | Brock et al. | |
| 2001/0001812 A1 | 5/2001 | Valley et al. | |
| 2001/0010247 A1 | 8/2001 | Snow | |
| 2002/0029783 A1 | 3/2002 | Stevens et al. | |

(56) References Cited

U.S. PATENT DOCUMENTS

| | | | |
|---|---|---|---|
| 2002/0042620 A1 | 4/2002 | Julian et al. | |
| 2002/0068922 A1 | 6/2002 | Peters | |
| 2002/0087157 A1 | 7/2002 | Sliwa et al. | |
| 2003/0050628 A1* | 3/2003 | Whitman et al. | 606/1 |
| 2008/0262654 A1* | 10/2008 | Omori et al. | 700/245 |

FOREIGN PATENT DOCUMENTS

| | | |
|---|---|---|
| DE | 4213426 | 10/1992 |
| DE | 4312147 | 10/1992 |
| DE | 4441333 | 5/1996 |
| EP | 0593920 | 4/1974 |
| EP | 0093101 | 11/1983 |
| EP | 0116220 | 8/1984 |
| EP | 0121474 | 10/1984 |
| EP | 0156774 | 10/1985 |
| EP | 0216532 | 4/1987 |
| EP | 0399701 | 11/1990 |
| EP | 0514139 | 11/1992 |
| EP | 0536903 | 4/1993 |
| EP | 0539762 | 5/1993 |
| EP | 0552050 | 7/1993 |
| EP | 0598579 | 5/1994 |
| EP | 0621006 | 10/1994 |
| EP | 0634144 | 1/1995 |
| EP | 0705571 | 4/1996 |
| EP | 0947167 | 10/1999 |
| EP | 0653922 | 12/1999 |
| FR | 2660851 | 10/1991 |
| GB | 2022421 | 12/1979 |
| GB | 2031733 | 4/1980 |
| GB | 2044108 | 10/1980 |
| GB | 2180455 | 4/1987 |
| NL | 7711347 | 4/1979 |
| SU | 659146 | 4/1979 |
| WO | WO 82/03545 | 10/1982 |
| WO | WO 83/00992 | 3/1983 |
| WO | WO 90/05491 | 5/1990 |
| WO | WO 91/07136 | 5/1991 |
| WO | WO 92/16141 | 10/1992 |
| WO | WO 93/08754 | 5/1993 |
| WO | WO 93/14706 | 8/1993 |
| WO | WO 95/18572 | 7/1995 |
| WO | WO 95/35065 | 12/1995 |
| WO | WO 96/18344 | 6/1996 |
| WO | WO 96/23536 | 8/1996 |
| WO | WO 98/14129 | 4/1998 |
| WO | WO 99/20328 | 4/1999 |
| WO | WO 99/58076 | 11/1999 |
| WO | WO 00/72765 | 12/2000 |
| WO | WO 01/08572 | 2/2001 |
| WO | WO 01/62163 | 8/2001 |

* cited by examiner

ELECTRO-MECHANICAL SURGICAL DEVICE

CROSS-REFERENCE TO RELATED APPLICATIONS

This is a continuation of U.S. application Ser. No. 11/049,631, filed on Feb. 1, 2005, now issued as U.S. Pat. No. 8,357,144 on Jan. 22, 2013; which is a continuation of U.S. application Ser. No. 10/256,681, filed on Sep. 26, 2002, now issued as U.S. Pat. No. 6,849,071 on Feb. 1, 2005; and which is a divisional of U.S. application Ser. No. 09/723,715, filed on Nov. 28, 2000, now issued as U.S. Pat. No. 6,783,654 on Aug. 31, 2004.

U.S. application Ser. No. 09/723,715 is a continuation-in-part of U.S. application Ser. No. 09/324,451, filed on Jun. 2, 1999, now issued as U.S. Pat. No. 6,315,184 on Nov. 13, 2001; a continuation-in-part of U.S. application Ser. No. 09/324,452, filed on Jun. 2, 1999, now issued as U.S. Pat. No. 6,443,973 on Sep. 3, 2002; a continuation-in-part of U.S. application Ser. No. 09/351,534, filed on Jul. 12, 1999, now issued as U.S. Pat. No. 6,264,087 on Jul. 24, 2001; a continuation-in-part of U.S. application Ser. No. 09/510,923, filed on Feb. 22, 2000, now issued as U.S. Pat. No. 6,517,565 on Feb. 11, 2003; a continuation-in-part of U.S. application Ser. No. 09/510,927, filed on Feb. 22, 2000, now issued as U.S. Pat. No. 6,716,233 on Apr. 6, 2004; and a continuation-in-part of U.S. application Ser. No. 09/510,932, filed on Feb. 22, 2000, now issued as U.S. Pat. No. 6,491,201 on Dec. 10, 2002.

U.S. application Ser. No. 09/510,923 is a continuation-in-part of U.S. application Ser. No. 09/324,452, filed on Jun. 2, 1999, now issued as U.S. Pat. No. 6,443,973 on Sep. 3, 2002.

U.S. application Ser. No. 09/510,927 is a continuation-in-part of U.S. application Ser. No. 09/324,452, filed on Jun. 2, 1999, now issued as U.S. Pat. No. 6,443,973 on Sep. 3, 2002.

FIELD OF THE INVENTION

The present invention relates to an electromechanical surgical device.

BACKGROUND INFORMATION

The literature is replete with descriptions of surgical devices. For example, U.S. Pat. No. 4,705,038 to Sjostrom et al. describes a surgical system for powered instruments. The system includes a handpiece containing a motor and including a recess adapted to receive one of a plurality of surgical devices. A pair of reed switches is disposed within the recess, and each of the surgical devices includes one or two magnets adapted to actuate the reed switches in a particular combination when the device is assembled with the handpiece. The combination of reed switches activated by the magnets of the assembled handpiece and surgical device identifies to the system the surgical device so assembled with the handpiece. The number of possible surgical devices identifiable by this system is limited to the four possible combination of up to two magnets.

U.S. Pat. No. 4,995,877 to Ams et al. describes a device with a rotationally-driven surgical instrument. The device includes a hand-held element containing a driving motor for driving a tool insert. The device further includes a control unit having a storage unit for storing operational data manually set by the user of the device. Such data may be transferred to a code carrier, which is insertable into a plug-in facility.

U.S. Pat. No. 5,249,583 to Mallaby describes an electronic biopsy instrument with wiperless position sensors. A slotted disc and a cam are affixed to a drive shaft, which is driven by a motor. A pair of sensors is arranged so that each sensor is activated when the slot of the slotted disc is positioned over the sensor to thereby determine the position of a cannula and a stylet of the instrument. The sensors, slotted disc, cam, motor and rechargeable batteries for powering the instrument are contained within a housing of the instrument.

U.S. Pat. No. 5,383,880 to Hooven describes an endoscopic surgical system with sensing means. The instrument includes a motor disposed within a hand-held housing. A sensor is provided in the head of an instrument of the system for sensing the blood oxygen content of adjacent tissue.

Similarly, U.S. Pat. No. 5,395,033 to Byme et al. describes an endoscopic surgical instrument having a pair of jaws. A permanent magnet is disposed in a distal end of one of the jaws, and a magneto-resistive sensor is disposed in a distal end of the other one of the jaws. The magnet produces a magnetic field between the jaws, and the sensor measures the variations in the magnetic field so that the distance between the jaws may be determined.

U.S. Pat. No. 5,467,911 to Tsuruta et al. describes a surgical device for stapling and fastening body tissues. The device includes an operation section and an insertion section, which is detachably attachable to the operation section.

U.S. Pat. Nos. 5,518,163, 5,518,164 and 5,667,517, all to Hooven, describe an endoscopic surgical system, which includes a motor disposed in a handle portion. A sensing member, which is used to sense the blood oxygen content of adjacent tissue, is disposed in a head of the instrument. A contact is also provided in the head of the instrument. When a firing nut of the system has moved forward in the head to drive and form surgical staples disposed therein, the firing nut engages the contact, thereby reversing the motor to retract the firing nut.

U.S. Pat. No. 5,653,374 to Young et al., U.S. Pat. No. 5,779,130 to Alesi et al. and U.S. Pat. No. 5,954,259 to Viola et al. describe a self-contained powered surgical apparatus, which includes a motor assembly and power source disposed within a hand-held instrument body.

These instruments and systems described above suffer numerous disadvantages. For example, in several of the above-described instruments and systems, a motor is disposed within a handle of the instrument. Due to size considerations, these motors generally provide limited torque. In certain of the instruments and systems described above, a battery is provided within the handle for powering the motor. Such battery systems, however, provide limited electrical power to the motors, further limiting the torque output by the motors.

In addition, it is generally not possible to accurately ascertain the positions of the operative elements of the aforementioned instruments and systems.

A further disadvantage of the above-described instruments and systems is that such instruments and systems typically require manual manipulation and operation. When a motor is provided in the handle of such instruments, manual manipulation and operation is awkward and cumbersome to the operator.

It is therefore an object of the present invention to provide an electro-mechanical surgical device, in which a motor system is provided remote from the surgical instrument.

It is a further object of the present invention to provide an electromechanical surgical device, which is operable via a remote control unit.

It is another object of the present invention to provide an electromechanical surgical device, in which the relative position of the components thereof may be accurately determined.

It is still another object of the present invention to provide an electro-mechanical surgical device, which includes a plurality of operating programs or algorithms. Each operating program or algorithm corresponds to a respective surgical instrument or attachment attachable to the electromechanical surgical device.

SUMMARY

The above and other beneficial objects and advantages of the present invention are most effectively attained by providing an electromechanical surgical device as described herein. In one example embodiment, an electromechanical surgical device includes: a housing; an elongated shaft extending from the housing, a distal end of the elongated shaft being detachably coupleable to a surgical instrument; at least two axially rotatable drive shafts disposed within the elongated shaft, a distal end of each of the drive shafts being configured to couple with the surgical instrument; a steering cable arrangement being configured to steer the distal end of the elongated shaft; and a motor system disposed within the housing and configured to drive the drive shafts and the steering cable arrangement.

In another example embodiment, the electromechanical surgical device includes a control system and a remote control unit configured to communicate with the control system to control the motor system via the control system. The remote control unit may include a wired remote control unit and/or a wireless remote control unit.

In yet another example embodiment, the electromechanical surgical device includes a sensor configured to detect the rotation of the drive shaft. The control system is configured to determine a position of the elements of the surgical instrument based on the detected rotation of the drive shaft.

In still another example embodiment, the electromechanical surgical device includes a first memory unit configured to store a plurality of operating programs or algorithms, each corresponding to a respective type of surgical instrument. The control system is configured to detect the type of surgical instrument attached to the electromechanical surgical device and to select or read the operating program or algorithm corresponding to the attached surgical instrument.

DETAILED DESCRIPTION

Figure 1:
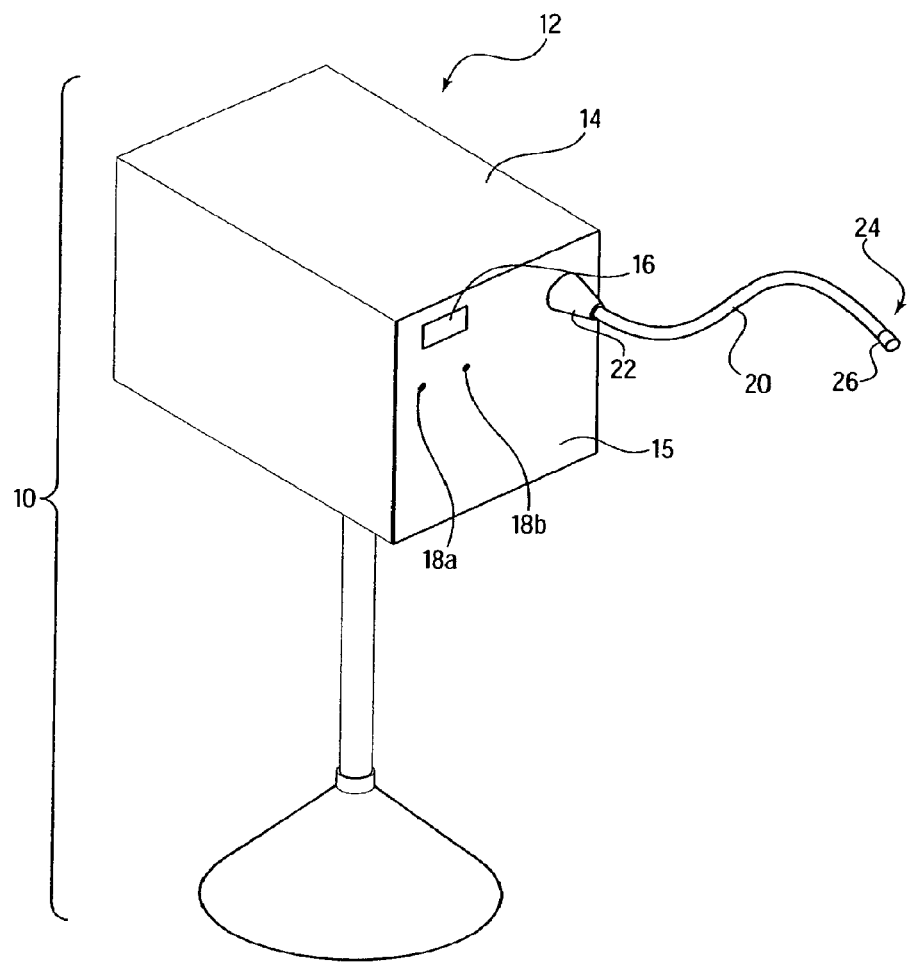
FIG. 1 is a perspective view of an electromechanical surgical device according to the present invention.

Those skilled in the art will gain an appreciation of the present invention from a reading of the following description when viewed in conjunction with the accompanying drawings of FIGS. 1-16, inclusive. The individual reference characters designate the same or similar elements throughout the several views.

Referring to FIG. 1, there is seen a perspective view of an electro-mechanical surgical device 10 according to an example embodiment of the present invention. Electro-mechanical surgical device 10 may include, for example, a remote power console 12, which includes a housing 14 having a front panel 15. Mounted on front panel 15 are a display device 16 and indicators 18a, 18b, which are more fully described hereinbelow. A flexible shaft 20 may extend from housing 14 and may be detachably secured thereto via a first coupling 22. The distal end 24 of flexible shaft 20 may include a second coupling 26 adapted to detachably secure a surgical instrument or attachment to the distal end 24 of flexible shaft 20. The surgical instrument or attachment may be, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. patent application Ser. No. 09/324,451, entitled "A Stapling Device for Use with an Electromechanical Driver Device for Use with Anastomosing, Stapling, and Resecting Instruments," now U.S. Pat. No. 6,315,184; U.S. patent application Ser. No. 09/324,452, entitled "Electromechanical Driver Device for Use with Anastomosing, Stapling, and Resecting Instruments," now U.S. Pat. No. 6,443,973; U.S. patent application Ser. No. 09/351,534, entitled "Automated Surgical Stapling System," now U.S. Pat. No. 6,264,087; U.S. patent application Ser. No. 09/510,926, entitled "A Vessel and Lumen Expander Attachment for Use with an Electromechanical Driver Device," now U.S. Pat. No. 6,348,061; U.S. patent application Ser. No. 09/510,927, entitled "Electromechanical Driver and Remote Surgical Instruments Attachment Having Computer Assisted Control Capabilities," now U.S. Pat. No. 6,716,233; U.S. patent application Ser. No. 09/510,931, entitled "A Tissue Stapling Attachment for Use with an Electromechanical Driver Device," now U.S. Pat. No. 6,533,157; U.S. patent application Ser. No. 09/510,932, entitled "A Fluid Delivery Mechanism for Use with Anastomosing, Stapling, and Resecting Instruments," now U.S. Pat. No. 6,491,201; and U.S. patent application Ser. No. 09/510,933, entitled "A Fluid Delivery Device for Use with Anastomosing, Stapling, and Resecting Instruments," now U.S. Pat. No. 6,488,197; each of which is expressly incorporated herein in its entirety by reference thereto.

Figure 2:
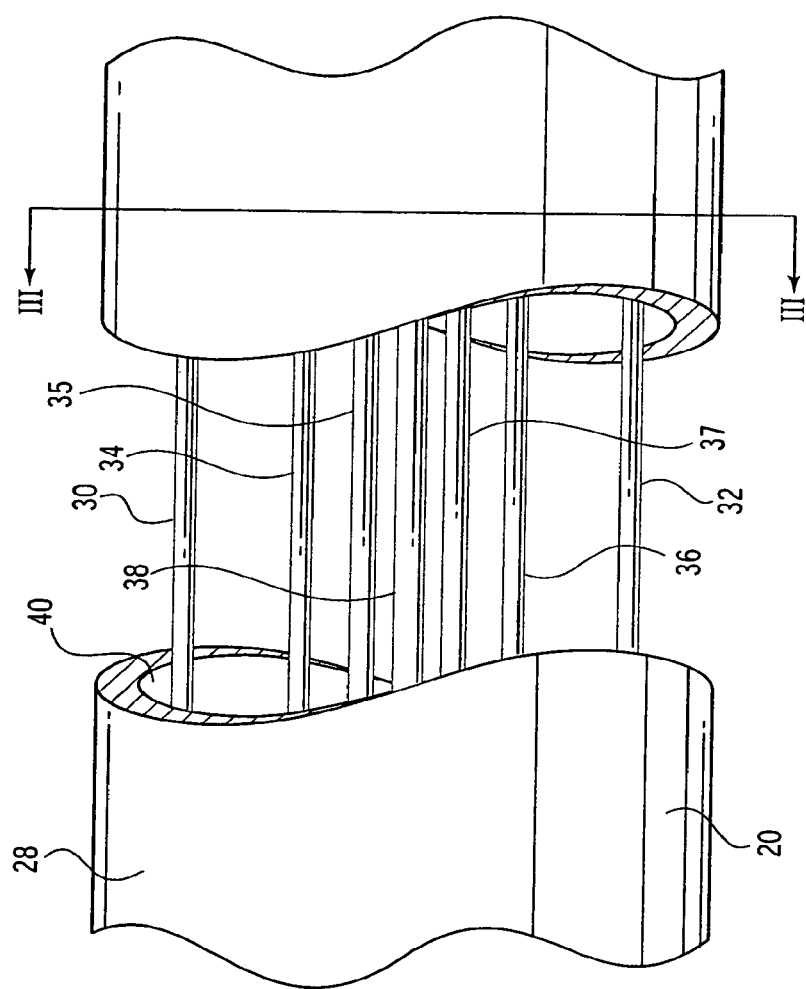
FIG. 2 is a side elevational view, partially in section, of a flexible shaft of the electromechanical surgical device illustrated in FIG. 1.
Figure 3:
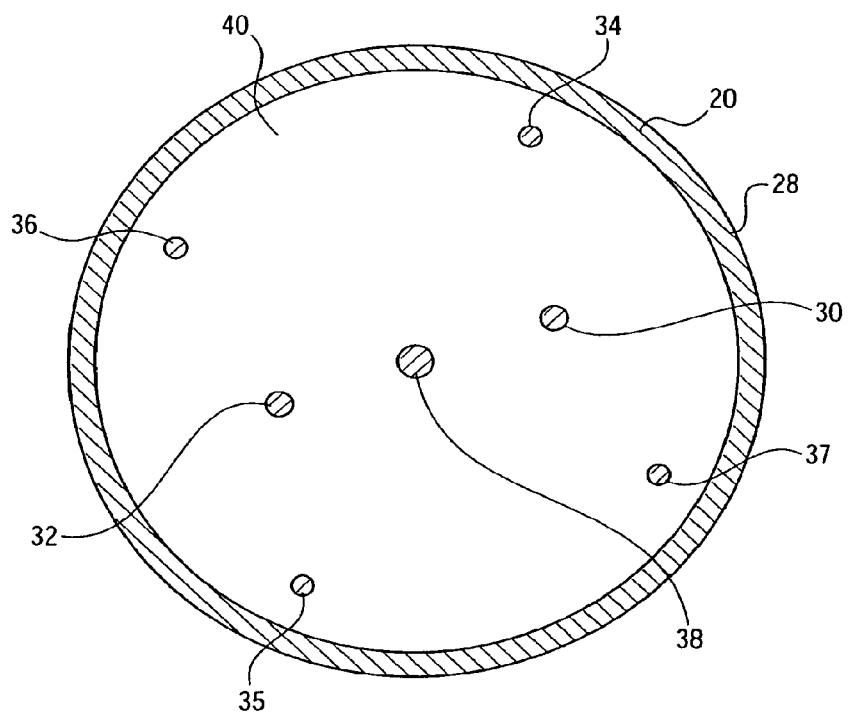
FIG. 3 is a cross-sectional view of the flexible shaft taken along the line 3-3 shown in FIG. 2.

Referring to FIG. 2, there is seen a side view, partially in section, of flexible shaft 20. According to one embodiment, flexible shaft 20 includes a tubular sheath 28, which may include a coating or other sealing arrangement to provide a fluid-tight seal between the interior channel 40 thereof and the environment. Sheath 28 may be formed of a tissue-compatible, sterilizable elastomeric material. The sheath 28 may also be formed of a material that is autoclavable. Disposed within the interior channel 40 of flexible shaft 20, and extending along the entire length thereof, may be a first rotatable drive shaft 30, a second rotatable drive shaft 32, a first steering cable 34, a second steering cable 35, a third steering cable 36, a fourth steering cable 37 and a data transfer cable 38. FIG. 3 is a cross-sectional view of flexible shaft 20 taken along the line 3-3 shown in FIG. 2 and further illustrates the several cables 30, 32, 34, 35, 36, 37, 38. Each distal end of the steering cables 34, 35, 36, 37 is affixed to the distal end 24 of the flexible shaft 20. Each of the several cables 30, 32, 34, 35, 36, 37, 38 may be contained within a respective sheath.

Figure 4:
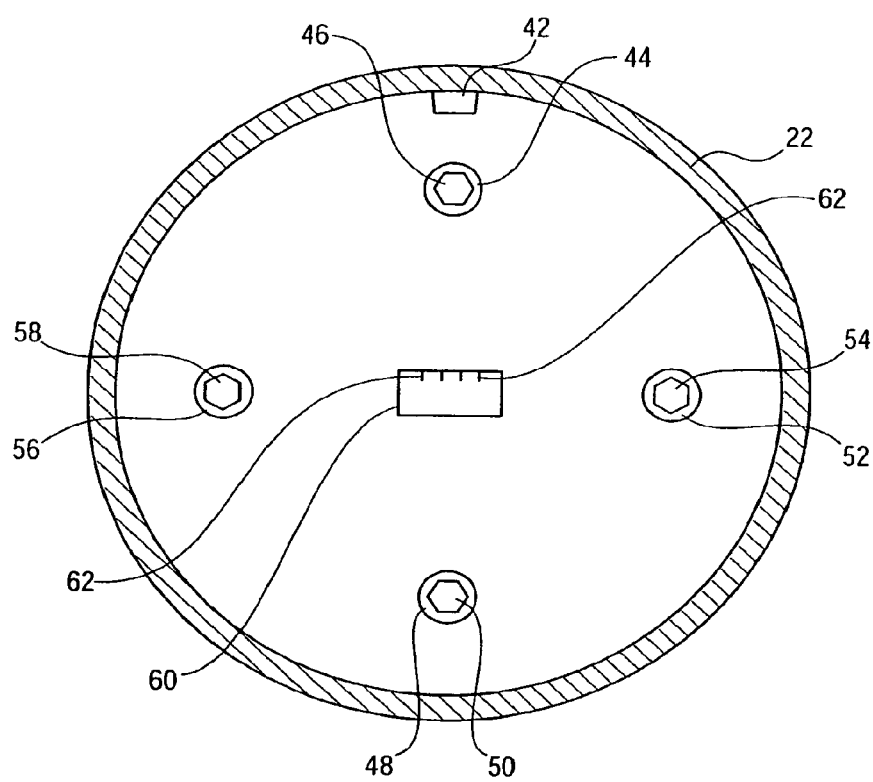
FIG. 4 is a rear end view of a first coupling of the flexible shaft illustrated in FIG. 2.

Referring now to FIG. 4, there is seen a rear end view of first coupling 22. First coupling 22 includes a first connector 44, a second connector 48, a third connector 52 and a fourth connector 56, each rotatably secured to first coupling 22. Each of the connectors 44, 48, 52, 56 includes a respective recess 46, 50, 54, 58. As shown in FIG. 4, each recess 46, 50, 54, 58 may be hexagonally shaped. It should be appreciated, however, that the recesses 46, 50, 54, 58 may have any shape and configuration to non-rotatably couple and rigidly attach the connectors 44, 48, 52, 56 to respective drive shafts of the motor arrangement contained within the housing 12, as more fully described below. It should be appreciated that complementary projections may be provided on respective drive shafts of the motor arrangement to thereby drive the drive elements of the flexible shaft 20 as described below. It should also be appreciated that the recesses may be provided on the drive shafts and complementary projections may be provided on the connectors 44, 48, 52, 56. Any other coupling arrangement configured to non-rotatably and releasably couple the connectors 44, 48, 52, 56 and the drive shafts of the motor arrangement may be provided.

One of the connectors 44, 48, 52, 56 is non-rotatably secured to the first drive shaft 30, and another one of the connectors 44, 48, 52, 56 is non-rotatably secured to the second drive shaft 32. The remaining two of the connectors 44, 48, 52, 56 engage with transmission elements configured to apply tensile forces on the steering cables 34, 35, 36, 37 to thereby steer the distal end 24 of the flexible shaft 20. The data transfer cable 38 is electrically and logically connected with data connector 60. Data connector 60 includes, for example, electrical contacts 62, corresponding to and equal in number to the number of individual wires contained in the data cable 38. First coupling 22 includes a key structure 42 to properly orient the first coupling 22 to a mating and complementary coupling arrangement disposed on the housing 12. Such key structure 42 may be provided on either one, or both, of the first coupling 22 and the mating and complementary coupling arrangement disposed on the housing 12. First coupling 22 may include a quick-connect type connector, which may use, for example, a simple pushing motion to engage the first coupling 22 to the housing 12. Seals may be provided in conjunction with any of the several connectors 44, 48, 52, 56, 60 to provide a fluid-tight seal between the interior of first coupling 22 and the environment.

Figure 5:
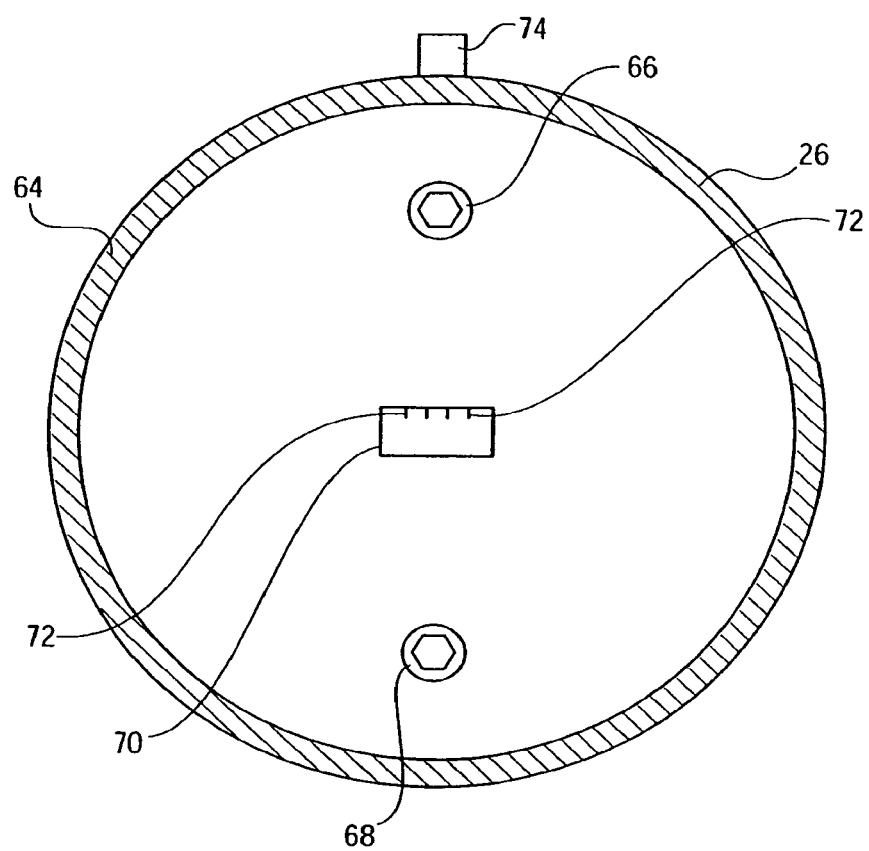
FIG. 5 is a front end view of a second coupling of the flexible shaft illustrated in FIG. 2.

Referring now to FIG. 5, there is seen a front end view of the second coupling 26 of flexible shaft 20. Second coupling 26 includes a first connector 66 and a second connector 68, each being rotatably secured to the second coupling 26 and each being non-rotatably secured to a distal end of a respective one of the first and second drive shafts 30, 32. A quick-connect type fitting 64 is provided on the second coupling 26 for detachably securing the surgical instrument or attachment thereto. The quick-connect type fitting 64 may be, for example, a rotary quick-connect type fitting, a bayonet type fitting, etc. A key structure 74 is provided on the second coupling 26 for properly aligning the surgical instrument or attachment to the second coupling 26. The key structure or other arrangement for properly aligning the surgical instrument or attachment to the flexible shaft 20 may be provided on either one, or both, of the second coupling 26 and the surgical instrument or attachment. In addition, the quick-connect type fitting may be provided on the surgical instrument or attachment. A data connector 70, having electrical contacts 72, is also provided in the second coupling 26. Like the data connector 60 of first coupling 22, the data connector 70 of second coupling 26 includes contacts 72 electrically and logically connected to the respective wires of data transfer cable 38 and contacts 62 of data connector 60. Seals may be provided in conjunction with the connectors 66, 68, 70 to provide a fluid-tight seal between the interior of second coupling 26 and the environment.

Disposed within housing 14 of the remote power console 12 are electro-mechanical driver elements configured to drive the drive shafts 30, 32 and the steering cables 34, 35, 36, 37 to thereby operate the electromechanical surgical device 10 and the surgical instrument or attachment attached to the second coupling 26. In the example embodiment illustrated schematically in FIG. 6, five electric motors 76, 80, 84, 90, 96, each operating via a power source, may be disposed in the remote power console 12. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 6:
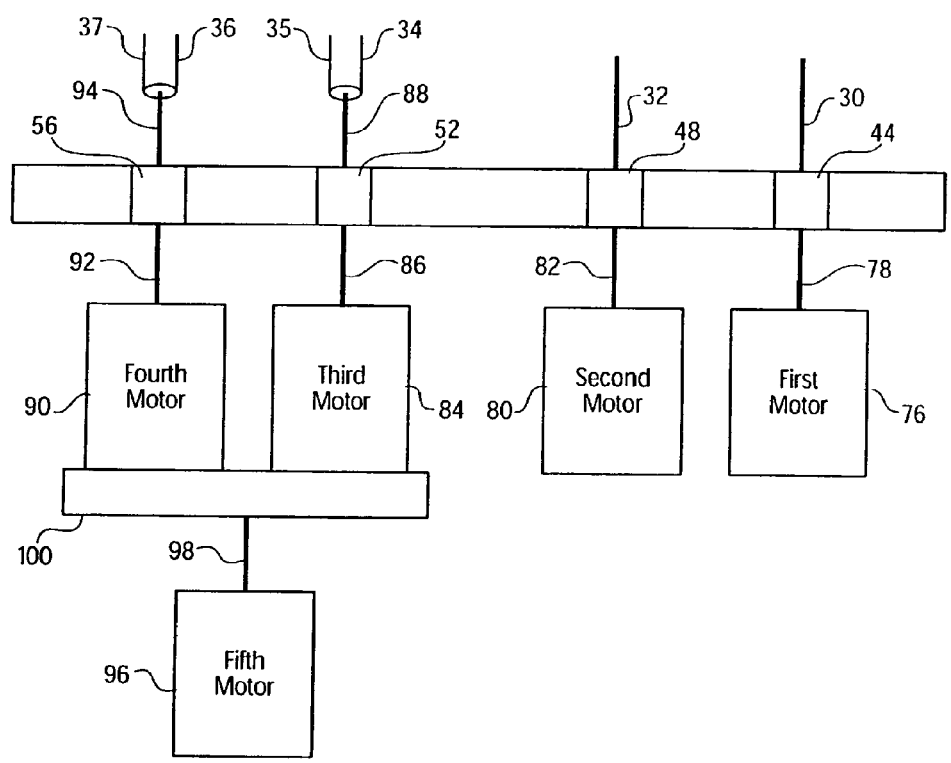
FIG. 6 is a schematic view illustrating a motor arrangement of the electro-mechanical surgical device illustrated in FIG. 1.

FIG. 6 illustrates schematically one possible arrangement of motors. An output shaft 78 of a first motor 76 engages with the first connector 44 of the first coupling 22 when the first coupling 22, and, therefore, flexible shaft 20, is engaged with the housing 14 to thereby drive the first drive shaft 30 and first connector 66 of second coupling 26. Similarly, an output shaft 82 of a second motor 80 engages the second connector 48 of first coupling 22 when first coupling 22, and, therefore, flexible shaft 20 is engaged with the housing 14 to thereby drive the second drive shaft 32 and second connector 68 of second coupling 26. An output shaft 86 of a third motor 84 engages the third connector 52 of the first coupling 22 when the first coupling 22, and, therefore, flexible shaft 20, is engaged with the housing 14 to thereby drive the first and second steering cables 34, 35 via a first pulley arrangement 88. An output shaft 92 of a fourth motor 90 engages the fourth connector 56 of the first coupling 22 when the first coupling 22, and, therefore, flexible shaft 20, is engaged with the housing 14 to thereby drive the third and fourth steering cables 36, 37 via a second pulley arrangement 94. The third and fourth motors 84, 90 may be secured on a carriage 100, which is selectively movable via an output shaft 98 of a fifth motor 96 between a first position and a second position to selectively engage and disengage the third and fourth motors 84, 90 with the respective pulley arrangement 88, 94 to thereby permit the flexible shaft 20 to become taut and steerable or limp as necessary. It should be appreciated that other mechanical, electrical or electromechanical mechanisms may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," now U.S. Pat. No. 6,517,565; which is expressly incorporated herein in its entirety by reference thereto.

Figure 7:
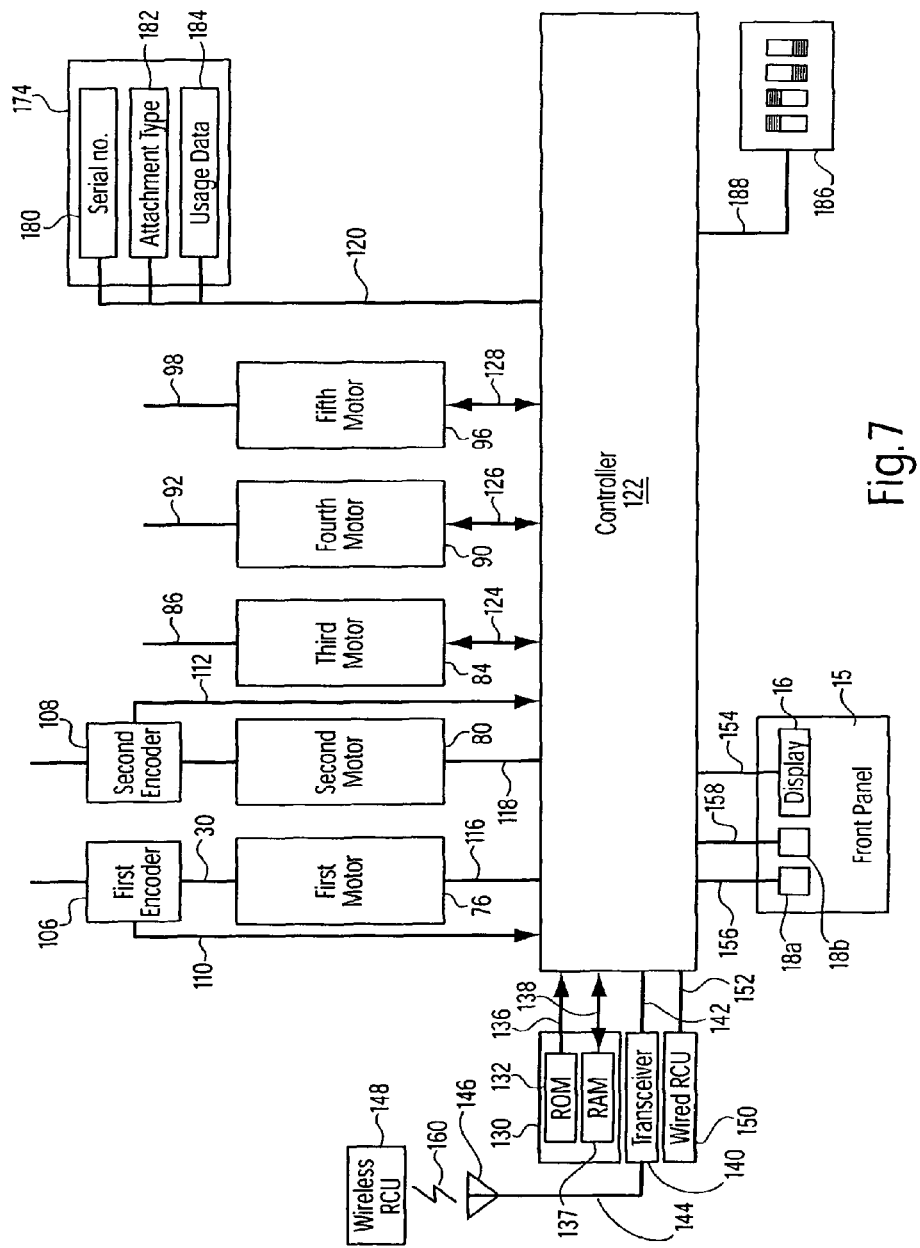
FIG. 7 is a schematic view of the electromechanical surgical device illustrated in FIG. 1.

Referring now to FIG. 7, there is seen a schematic view of the electro-mechanical surgical device 10. A controller 122 is provided in the housing 14 of remote power console 12 and is configured to control all functions and operations of the electromechanical surgical device 10 and any surgical instrument or attachment attached to the flexible shaft 20. A memory unit 130 is provided and may include memory devices, such as, a ROM component 132 and/or a RAM component 134. ROM component 132 is in electrical and logical communication with controller 122 via line 136, and RAM component 134 is in electrical and logical communication with controller 122 via line 138. RAM component 134 may include any type of random-access memory, such as, for example, a magnetic memory device, an optical memory device, a magneto-optical memory device, an electronic memory device, etc. Similarly, ROM component 132 may include any type of read-only memory, such as, for example, a removable memory device, such as a PC-Card or PCMCIA-type device. It should be appreciated that ROM component 132 and RAM component 134 may be embodied as a single unit or may be separate units and that ROM component 132 and/or RAM component 134 may be provided in the form of a PC-Card or PCMCIA-type device. Controller 122 is further connected to front panel 15 of housing 14 and, more particularly, to display device 16 via line 154 and indicators 18a, 18b via respective lines 156, 158. Lines 116, 118, 124, 126, 128 electrically and logically connect controller 122 to first, second, third, fourth and fifth motors 76, 80, 84, 90, 96, respectively. A wired remote control unit ("RCU") 150 is electrically and logically connected to controller 122 via line 152. A wireless RCU 148 is also provided and communicates via a wireless link 160 with a receiving/sending unit 146 connected via line 144 to a transceiver 140. The transceiver 140 is electrically and logically connected to controller 122 via line 142. Wireless link 160 may be, for example, an optical link, such as an infrared link, a radio link or any other form of wireless communication link.

A switch device 186, which may be, for example, an array of DIP switches, may be connected to controller 122 via line 188. Switch device 186 may be used, for example, to select one of a plurality of languages used in displaying messages and prompts on the display device 16. The messages and prompts may relate to, for example, the operation and/or the status of the electromechanical surgical device 10 and/or to any surgical instrument or attachment attached thereto.

According to the example embodiment of the present invention, a first encoder 106 is provided within the second coupling 26 and is configured to output a signal in response to and in accordance with the rotation of the first drive shaft 30. A second encoder 108 is also provided within the second coupling 26 and is configured to output a signal in response to and in accordance with the rotation of the second drive shaft 32. The signal output by each of the encoders 106, 108 may represent the rotational position of the respective drive shaft 30, 32 as well as the rotational direction thereof. Such encoders 106, 108 may be, for example, Hall-effect devices, optical devices, etc. Although the encoders 106, 108 are described as being disposed within the second coupling 26, it should be appreciated that the encoders 106, 108 may be provided at any location between the motor system and the surgical instrument or attachment.

Figure 8:
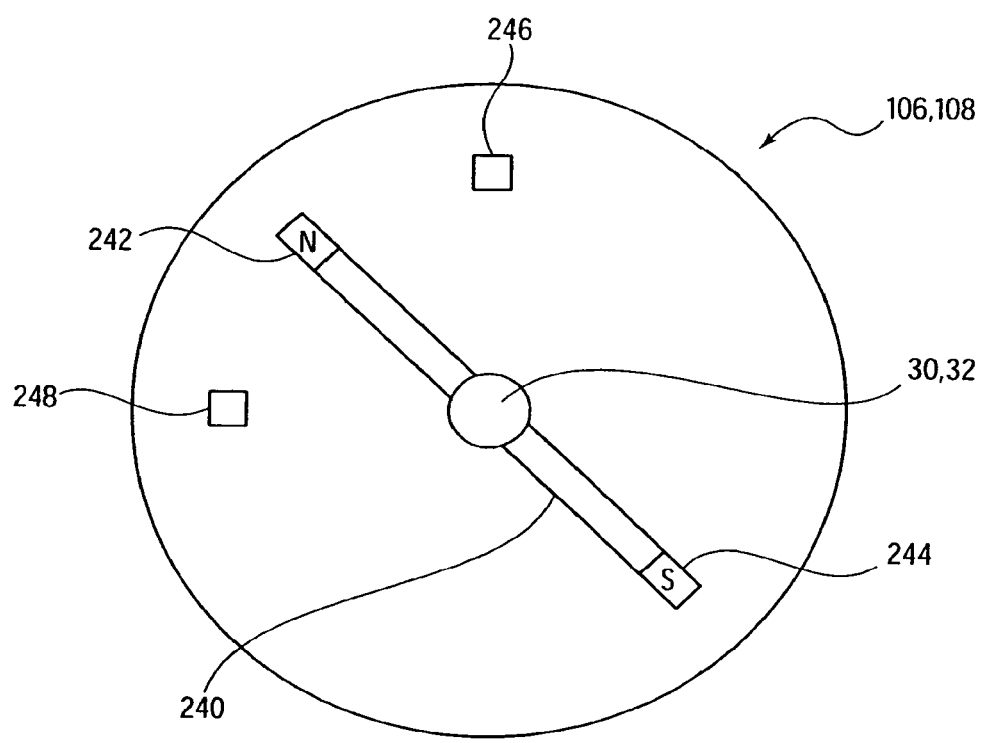
FIG. 8 is a schematic view of an encoder of the flexible shaft illustrated in FIGS. 2 and 3.

FIG. 8 is a schematic view of an encoder 106, 108, which includes a Hall-effect device. Mounted non-rotatably on drive shaft 30, 32 is a magnet 240 having a north pole 242 and a south pole 244. The encoder 106, 108 further includes a first sensor 246 and second sensor 248, which are disposed approximately 90° apart relative to the longitudinal, or rotational, axis of drive shaft 30, 32. The output of the sensors 246, 248 is persistent and changes its state as a function of a change of polarity of the magnetic field in the detection range of the sensor. Thus, based on the output signal from the encoders 106, 108, the angular position of the drive shaft 30, 32 may be determined within one-quarter revolution and the direction of rotation of the drive shaft 30, 32 may be determined. The output of each encoder 106, 108 is transmitted via a respective line 110, 112 of data transfer cable 38 to controller 122. The controller 122, by tracking the angular position and rotational direction of the drive shafts 30, 32 based on the output signal from the encoders 106, 108, can thereby determine the position and/or state of the components of the surgical instrument or attachment connected to the electromechanical surgical device 10. That is, by counting the revolutions of the drive shaft 30, 32, the controller 122 can determine the position and/or state of the components of the surgical instrument or attachment connected to the electromechanical surgical device 10.

Figure 9:
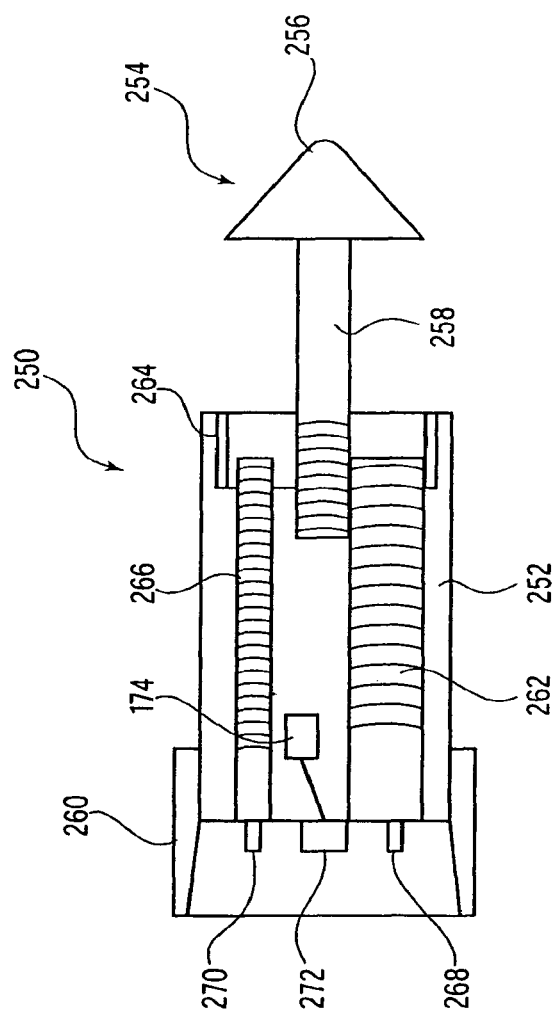
FIG. 9 is a schematic cross-sectional side view of an exemplary circular surgical stapler attachment used in connection with the electromechanical surgical device illustrated in FIG. 1.

For example, in a circular surgical stapler attachment 250, such as that shown schematically in cross-section in FIG. 9, the circular surgical stapler attachment 250 includes a coupling 260 adapted by size and configuration to cooperate with the second coupling 26 of flexible shaft 20 to detachably attach the circular surgical stapler attachment 250 thereto. Circular surgical stapler attachment 250 includes an anvil portion 254 having an anvil 256 mounted on the distal end of an anvil stem 258. The anvil stem 258 is extended and retracted by the operation of an anvil drive shaft 262, which is rotatably secured within the body portion 252 of the circular surgical stapler attachment 250. A proximal end of the anvil drive shaft 262 includes a first connector 268 adapted by size and configuration to couple with the first connector 66 of second coupling 26. Circular surgical stapler attachment 250 further includes a staple driver/cutter 264 driven by the rotation of a staple driver/cutter drive shaft 266. The proximal end of the staple driver/cutter drive shaft 266 includes a second connector 270, which is adapted by size and configuration to couple with the second connector 68 of second coupling 26. Thus, in the example circular surgical stapler attachment 250 shown in FIG. 9, the extension and retraction of the anvil 256 is effected by the operation of the first motor 76, and the extension and retraction of the staple driver/cutter 264 is effected by the operation of the second motor 80. The pitch of the anvil drive shaft 262 and the pitch of the stapler driver/cutter drive shaft 266 are predetermined and known quantities. That is, the advancement distance of the anvil 256 and the staple driver/cutter 264 are functions of, and ascertainable on the basis of, the rotation of the respective drive shaft 30, 32. By ascertaining an absolute position of the anvil 256 and the staple driver/cutter 264 at a point in time, the relative displacement of the anvil 256 and staple driver/cutter 264, based on the output signal from the encoders 106, 108 and the known pitches of the anvil drive shaft 262 and staple driver/cutter drive shaft 266, may be used to ascertain the absolute position of the anvil 256 and staple driver/cutter 264 at all times thereafter. The absolute position of the anvil 256 and staple driver/cutter 264 may be fixed and ascertained at the time that the circular surgical stapler attachment 250 is first coupled to the flexible shaft 20. Alternatively, the position of the anvil 256 and the staple driver/cutter 264 relative to, for example, the body portion 252 may be determined based on the output signal from the encoders 106, 108.

Circular surgical stapler attachment 250 further includes a data connector 272 adapted by size and configuration to electrically and logically connect to connector 70 of second coupling 26. In the example embodiment, data connector 272 includes contacts (not shown) equal in number to the number of leads 72 of connector 70. Contained within the circular surgical stapler attachment 250 is a memory unit 174 electrically and logically connected with the data connector 272. Memory unit 174 may be in the form of, for example, an EEPROM, EPROM, etc. and may be contained, for example, within the body portion 252 of circular surgical stapler attachment 250.

Figure 10:
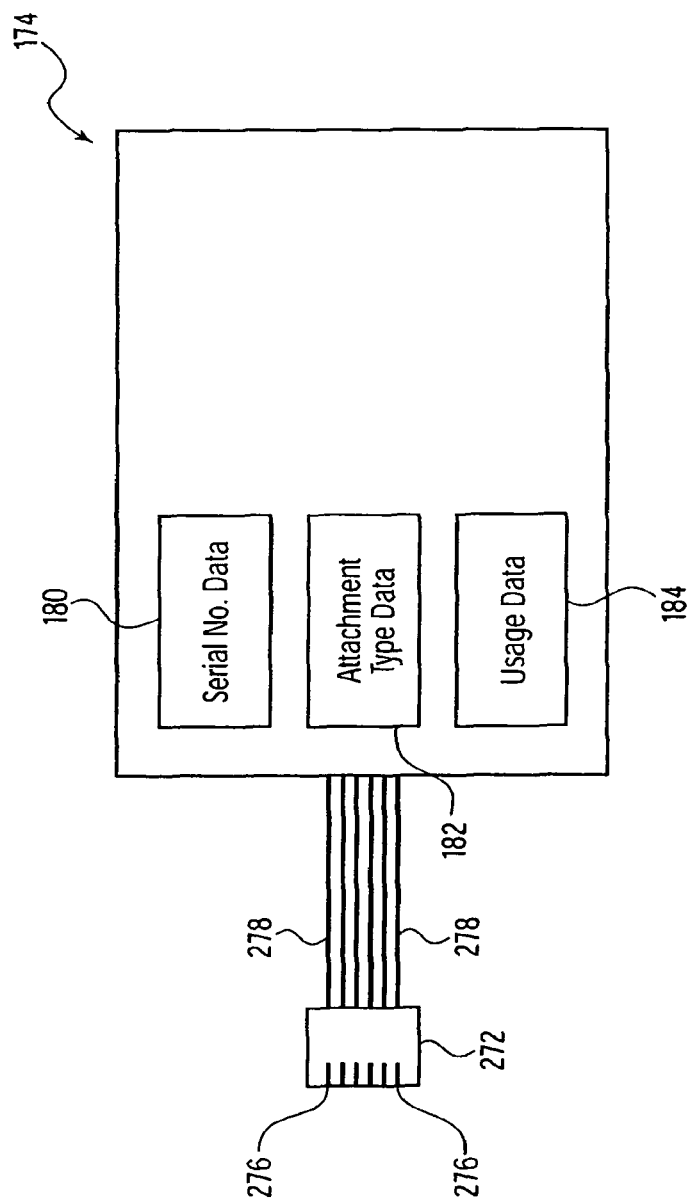
FIG. 10 is a schematic view of a memory device of the exemplary circular surgical stapler attachment illustrated in FIG. 9.

FIG. 10 schematically illustrates the memory unit 174. As seen in FIG. 10, data connector 272 includes contacts 276, each electrically and logically connected to memory unit 174 via a respective line 278. Memory unit 174 is configured to store, for example, a serial number data 180, an attachment type identifier (ID) data 182 and a usage data 184. Memory unit 174 may additionally store other data. Both the serial number data 180 and the ID data 182 may be configured as read-only data. In the example embodiment, serial number data 180 is data uniquely identifying the particular surgical instrument or attachment, whereas the ID data 182 is data identifying the type of the attachment, such as, for example, a circular surgical stapler attachment, a linear surgical stapler attachment, etc. The usage data 184 represents usage of the particular attachment, such as, for example, the number of times the anvil 256 of the circular surgical stapler attachment 250 has been advanced or the number of times that the staple driver/cutter 264 of the circular surgical stapler attachment 250 has been advanced or fired.

It should be appreciated that each types of surgical instrument or attachment attachable to the distal end 24 of the flexible shaft 20 may be designed and configured to be used a single time or multiple times. The surgical instrument or attachment may also be designed and configured to be used a predetermined number of times. Accordingly, the usage data 184 may be used to determine whether the surgical instrument or attachment has been used and whether the number of uses has exceeded the maximum number of permitted uses. As more fully described below, an attempt to use a surgical instrument or attachment after the maximum number of permitted uses has been reached will generate an ERROR condition.

It should be appreciated that the circular surgical stapler attachment 250 illustrated in FIG. 9 is intended to be merely an example of a surgical attachment used in conjunction with the electro-mechanical surgical device 10. It should be further appreciated that any other type of surgical instrument or attachment, such as those enumerated hereinabove, may be used in conjunction with the electro-mechanical surgical device 10. Regardless of the particular type of surgical instrument or attachment, in the example embodiment of the present invention, the surgical instrument or attachment includes the coupling elements 268, 270, 272, as necessary for proper operation of the surgical instrument or attachment, as well as the memory unit 174. Although the drive shafts and motors are described herein as effecting particular functions of the circular surgical stapler attachment 250, it should be appreciated that the drive shafts and motors may effect the same or other functions of other types of surgical instruments or attachments.

Referring again to FIG. 7, in accordance with the example embodiment of the present invention, the controller 122 is configured to read the ID data 182 from the memory unit 174 of the surgical instrument or attachment when the surgical instrument or attachment is initially connected to the flexible shaft 20. The memory unit 174 is electrically and logically connected to the controller 122 via line 120 of data transfer cable 38. Based on the read ID data 182, the controller 122 is configured to read or select from the memory unit 130, an operating program or algorithm corresponding to the type of surgical instrument or attachment connected to the flexible shaft 20. The memory unit 130 is configured to store the operating programs or algorithms for each available type of surgical instrument or attachment, the controller 122 selecting and/or reading the operating program or algorithm from the memory unit 130 in accordance with the ID data 182 read from the memory unit 174 of an attached surgical instrument or attachment. As indicated above, the memory unit 130 may include a removable ROM component 132 and/or RAM component 134. Thus, the operating programs or algorithms stored in the memory unit 130 may be updated, added, deleted, improved or otherwise revised as necessary. It should be appreciated that the serial number data 180 and/or usage data 184 may also be used to determine which of a plurality of operating programs or algorithms is read or selected from the memory unit 130. It should also be appreciated that the operating program or algorithm may alternatively be stored in the memory unit 174 of the surgical instrument or attachment and transferred to the controller 122 via the data transfer cable 38. Once the appropriate operating program or algorithm is read or selected by, or transmitted to, the controller 122, the controller 122 causes the operating program or algorithm to be executed in accordance with operations performed by the user via the wired RCU 150 and/or the wireless RCU 148. As indicated hereinabove, the controller 122 is electrically and logically connected with the first, second, third, fourth and fifth motors 76, 80, 84, 90, 96 via respective lines 116, 118, 124, 126, 128 and controls such motors 76, 80, 84, 90, 96 in accordance with the read, selected or transmitted operating program or algorithm via the respective lines 116, 118, 124, 126, 128.

Figure 11:
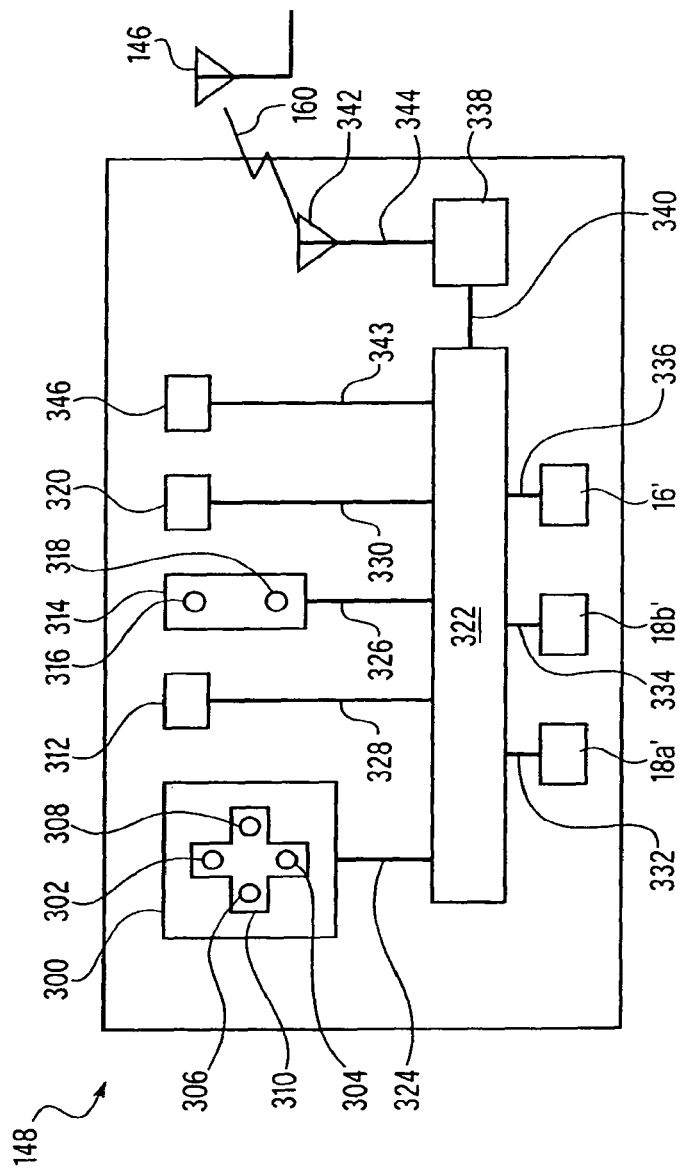
FIG. 11 is a schematic view of a wireless remote control unit of the electro-mechanical surgical device illustrated in FIG. 1.

Referring now to FIG. 11, there is seen a schematic view of wireless RCU 148. Wireless 148 includes a steering controller 300 having a plurality of switches 302, 304, 306, 308 arranged under a four-way rocker 310. The operation of switches 302, 304, via rocker 310, controls the operation of first and second steering cables 34, 35 via third motor 84. Similarly, the operation of switches 306, 308, via rocker 310, controls the operation of third and fourth steering cables 36, 37 via fourth motor 92. It should be appreciated that rocker 310 and switches 302, 304, 306, 308 are arranged so that the operation of switches 302, 304 steers the flexible shaft 20 in the north-south direction and that the operation of switches 306, 308 steers the flexible shaft 20 in the east-west direction. Reference herein to north, south, east and west is made to a relative coordinate system. Alternatively, a digital joystick, analog joystick, etc. may be provided in place of rocker 310 and switches 302, 304, 306, 308. Potentiometers or any other type of actuator may also be used in place of switches 302, 304, 306, 308.

Wireless RCU 148 further includes a steering engage/disengage switch 312, the operation of which controls the operation of fifth motor 96 to selectively engage and disengage the steering mechanism. Wireless RCU 148 also includes a two-way rocker 314 having first and second switches 316, 318 operable thereby. The operation of these switches 316, 318 controls certain functions of the electro-mechanical surgical device 10 and any surgical instrument or attachment attached to the flexible shaft 20 in accordance with the operating program or algorithm corresponding to the attached surgical instrument or attachment, if any. For example, where the surgical instrument is a circular surgical stapler attachment 250, such as that shown in FIG. 9 and described hereinabove, operation of the two-way rocker 314 may control the advancement and retraction of the anvil 256. Wireless RCU 148 is provided with yet another switch 320, the operation of which may further control the operation of the electromechanical surgical device 10 and any surgical instrument or attachment attached to the flexible shaft 20 in accordance with the operating program or algorithm corresponding to the attached surgical instrument or attachment, if any. For example, when the circular surgical stapler attachment 250 is attached to the flexible shaft 20, operation of the switch 320 initiates the advancement, or firing sequence, of the staple driver/cutter 264.

Wireless RCU 148 includes a controller 322, which is electrically and logically connected with the switches 302, 304, 306, 308 via line 324, with the switches 316, 318 via line 326, with switch 312 via line 328 and with switch 320 via line 330. Wireless RCU 148 may include indicators 18*a*', 18*b*', corresponding to the indicators 18*a*, 18*b* of front panel 15, and a display device 16', corresponding to the display device 16 of the front panel 15. If provided, the indicators 18*a*', 18*b*' are electrically and logically connected to controller 322 via respective lines 332, 334, and the display device 16' is electrically and logically connected to controller 322 via line 336. Controller 322 is electrically and logically connected to a transceiver 338 via line 340, and transceiver 338 is electrically and logically connected to a receiver/transmitter 342 via line 344. A power supply, not shown, for example, a battery, may be provided in wireless RCU 148 to power the same. Thus, the wireless RCU 148 may be used to control the operation of the electro-mechanical surgical device 10 and any surgical instrument or attachment attached to the flexible shaft 20 via wireless link 160.

Wireless RCU 148 may include a switch 346 connected to controller 322 via line 348. Operation of switch 346 transmits a data signal to the transmitter/receiver 146 via wireless link 160. The data signal includes identification data uniquely identifying the wireless RCU 148. This identification data is used by the controller 122 to prevent unauthorized operation of the electromechanical surgical device 10 and to prevent interference with the operation of the electromechanical surgical device 10 by another wireless RCU. Each subsequent communication between the wireless RCU 148 and the electromechanical device surgical 10 may include the identification data. Thus, the controller 122 can discriminate between wireless RCUs and thereby allow only a single, identifiable wireless RCU 148 to control the operation of the electromechanical surgical device 10 and any surgical instrument or attachment attached to the flexible shaft 20.

Based on the positions of the components of the surgical instrument or attachment attached to the flexible shaft 20, as determined in accordance with the output signals from the encoders 106, 108, the controller 122 may selectively enable or disable the functions of the electromechanical surgical device 10 as defined by the operating program or algorithm corresponding to the attached surgical instrument or attachment. For example, where the surgical instrument or attachment is the circular surgical stapler attachment 250 illustrated in FIG. 9, the firing function controlled by the operation of the switch 320 is disabled unless the space or gap between the anvil 256 and the body portion 252 is determined to be within an acceptable range. The space or gap between the anvil 256 and the body portion 252 is determined based on the output signal from the encoders 106, 108, as more fully described hereinabove. It should be appreciated that the switch 320 itself remains operable but that the controller 122 does not effect the corresponding function unless the space or gap is determined to be within the acceptable range.

Figure 12:
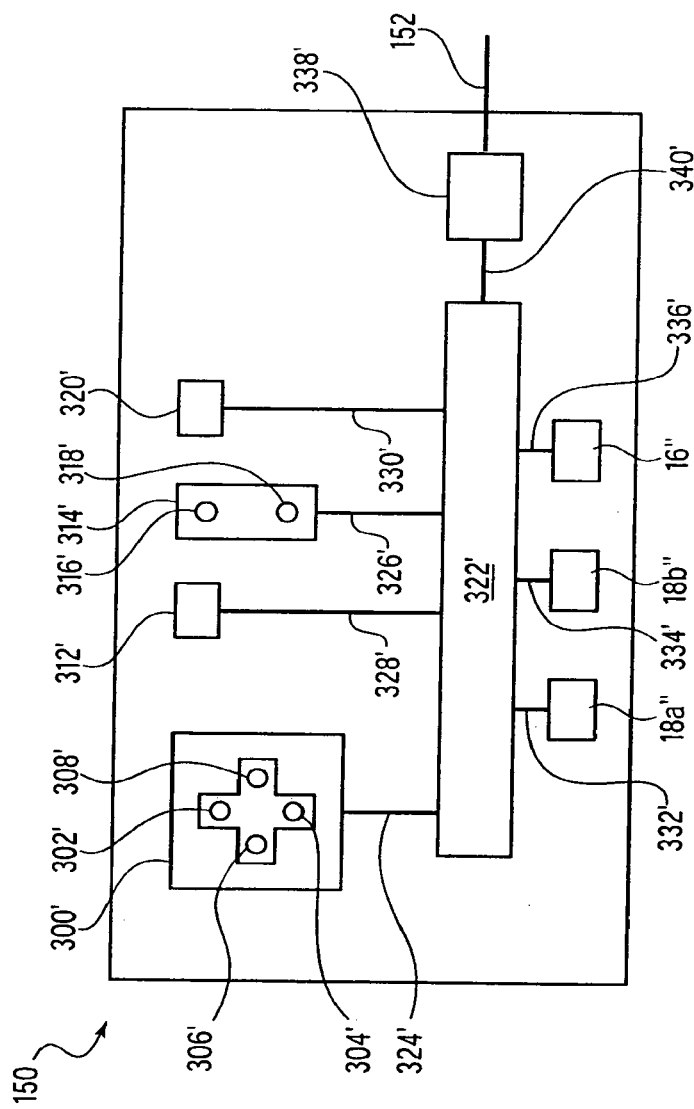
FIG. 12 is a schematic view of a wired remote control unit of the electro-mechanical surgical device illustrated in FIG. 1.

Referring now to FIG. 12, there is seen a schematic view of a wired RCU 150. In the example embodiment, wired RCU 150 includes substantially the same control elements as the wireless RCU 148 and further description of such elements is omitted. Like elements are noted in FIG. 12 with an accompanying prime. It should be appreciated that the functions of the electro-mechanical surgical device 10 and any surgical instrument or attachment attached to the flexible shaft 20 may be controlled by the wired RCU 150 and/or by the wireless RCU 148. In the event of a battery failure, for example, in the wireless RCU 148, the wired RCU 150 may be used to control the functions of the electro-mechanical surgical device 10 and any surgical instrument or attachment attached to the flexible shaft 20.

As described hereinabove, the front panel 15 of housing 14 includes display device 16 and indicators 18*a*, 18*b*. The display device 16 may include an alpha-numeric display device, such as an LCD display device. Display device 16 may also include an audio output device, such as a speaker, a buzzer, etc. The display device 16 is operated and controlled by controller 122 in accordance with the operating program or algorithm corresponding to a surgical instrument or attachment, if any, attached to the flexible shaft 20. If no surgical instrument or attachment is so attached, a default operating program or algorithm may be read or selected by, or transmitted to, controller 122 to thereby control the operation of the display device 16 as well as the other aspects and functions of the electro-mechanical surgical device 10. If the circular surgical stapler attachment 250 illustrated in FIG. 9 is attached to flexible shaft 20, display device 16 may display, for example, data indicative of the gap between the anvil 256 and the body portion 252 as determined in accordance with the output signal of encoders 106, 108, as more fully described hereinabove.

Similarly, the indicators 18*a*, 18*b* are operated and controlled by controller 122 in accordance with the operating program or algorithm corresponding to the surgical instrument or attachment, if any, attached to the flexible shaft 20. Indicator 18*a* and/or indicator 18*b* may include an audio output device, such as a speaker, a buzzer, etc., and/or a visual indicator device, such as an LED, a lamp, a light, etc. If the circular surgical stapler attachment 250 illustrated in FIG. 9 is attached to the flexible shaft 20, indicator 18*a* may indicate, for example, that the electromechanical surgical device 10 is in a power ON state, and indicator 18*b* may, for example, indicate whether the gap between the anvil 256 and the body portion 252 is determined to be within the acceptable range as more fully described hereinabove. It should be appreciated that although only two indicators 18*a*, 18*b* are described, any number of additional indicators may be provided as necessary. Additionally, it should be appreciated that although a single display device 16 is described, any number of additional display devices may be provided as necessary.

The display device 16' and indicators 18a', 18b' of wireless RCU 150 and the display device 16" and indicators 18a", 18b" of wired RCU 148 are similarly operated and controlled by respective controller 322, 322' in accordance with the operating program or algorithm corresponding to the surgical instrument or attachment, if any, attached to the flexible shaft 20.

Figure 13:
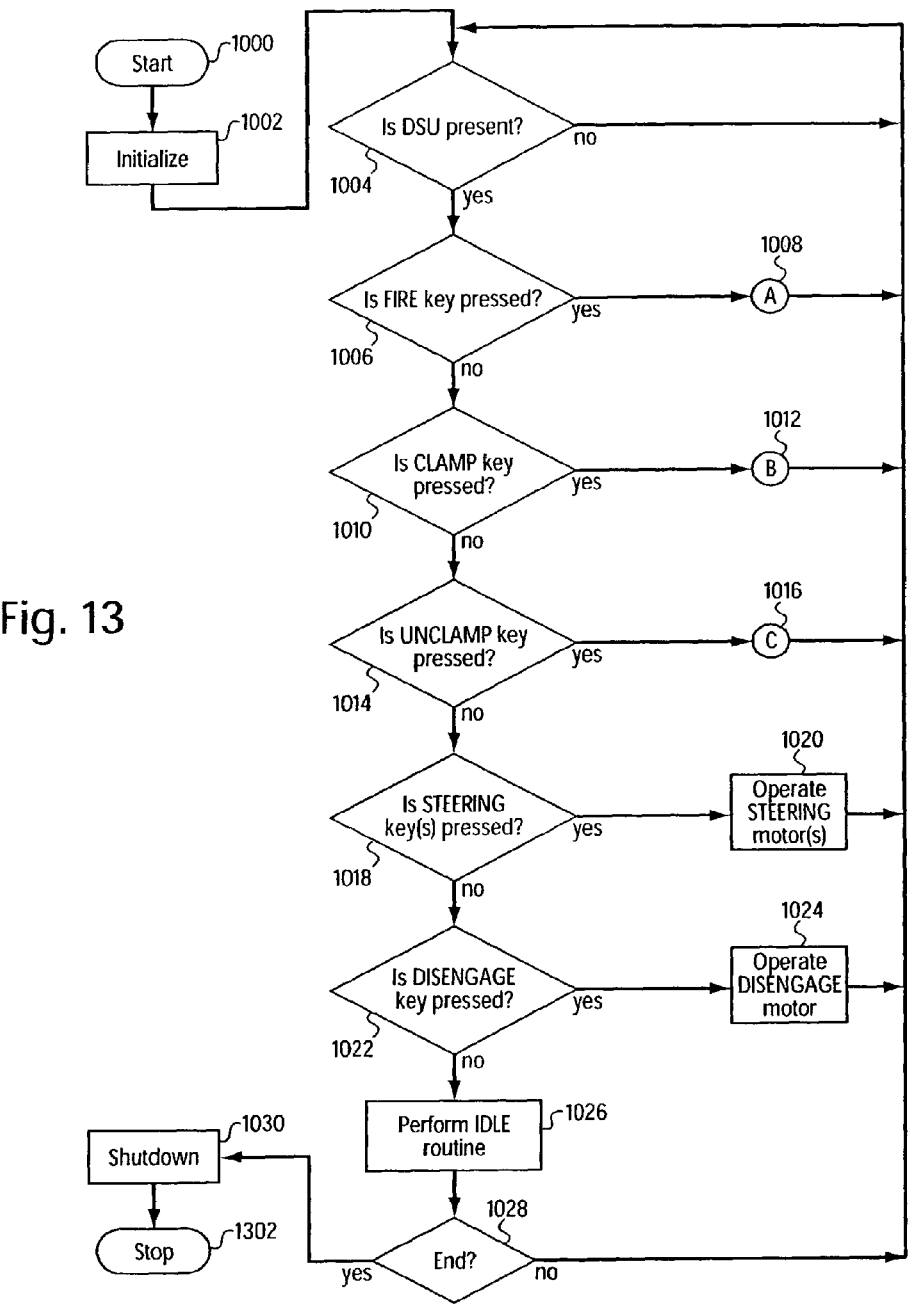
FIG. 13 illustrates a flowchart of a main operating program for operating the electromechanical surgical device illustrated in FIG. 1.

Referring now to FIG. 13, there is seen a flowchart of a main operating program according to the present invention. The main operating program begins at step 1000 and proceeds to step 1002, during which the electromechanical surgical device 10 is initialized. Step 1002 may include initialization steps, such as memory population and initialization, diagnostic self-testing, etc. After initialization step 1002, it is determined in step 1004 whether a surgical instrument or attachment ("DLU") is present—that is, installed on the distal end 24 of flexible shaft 20. If it is determined in step 1004 that no DLU is present, control is transferred to loop 1034. If it is determined that a DLU is present, the operating program proceeds to step 1006, in which it is determined whether the FIRE key is pressed. FIRE key, in this context, refers to one of the switches of the wireless RCU 148 and/or wired RCU 150. More particularly, the FIRE key may correspond to switch 320 of wireless RCU 148 and/or switch 320' of wired RCU 150. If it is determined in step 1006 that FIRE key is pressed, control is transferred to routine A in step 1008. Routine A is specific to the DLU, if any, attached to the flexible shaft 20. Routine A is more fully described hereinbelow and in FIGS. 14a-14d. After the execution of routine A in step 1008, control is transferred to loop 1034.

If it is determined in step 1006 that the FIRE key is not pressed, it is determined in step 1010 whether the CLAMP key is pressed. In this context, the CLAMP key refers to one of the switches of the wireless RCU 148 and/or wired RCU 150. More particularly, CLAMP switch may correspond to, for example, switch 316 of wireless RCU 148 and/or to switch 316' of wired RCU 150. If it is determined in step 1010 that CLAMP key is pressed, control is transferred to routine B in step 1012. Routine B is specific to the DLU, if any, attached to the flexible shaft 20. Routine B is more fully described hereinbelow and in FIGS. 15a and 15b. After the execution of routine B in step 1012, control is transferred to loop 1034.

If it is determined in step 1010 that the CLAMP key is not pressed, it is determined in step 1014 whether the UNCLAMP key is pressed. In this context, the UNCLAMP key refers to one of the switches of the wireless RCU 148 and/or wired RCU 150. More particularly, the UNCLAMP switch may correspond to, for example, switch 318 of wireless RCU 148 and/or to switch 318' of wired RCU 150. If it is determined in step 1014 that UNCLAMP key is pressed, control is transferred to routine C in step 1016. Routine C is specific to the DLU, if any, attached to the flexible shaft 20. Routine C is more fully described hereinbelow and in FIG. 16. After the execution of routine C in step 1016, control is transferred to loop 1034.

If it is determined in step 1014 that the UNCLAMP key is not pressed, it is determined in step 1018 whether one or more of STEERING keys are pressed. In this context, the STEERING keys refer to respective switches of the wireless RCU 148 and/or wired RCU 150. More particularly, the STEERING keys may correspond to switches 302, 304, 306, 308 of wireless RCU 148 and/or switches 302', 304', 306', 308' of wired RCU 150. If it is determined in step 1018 that one or more STEERING keys are pressed, operation of respective steering motor(s) is performed in step 1020. The steering motors may correspond to third motor 84 and fourth motor 92 as more fully set forth above. After the execution of step 1020, control is transferred to loop 1034.

If it is determined in step 1018 that none of the STEERING keys is pressed, it is determined in step 1022 whether the DISENGAGE key is pressed. In this context, the DISENGAGE key refers to one of the switches of wireless RCU 148 and/or wired RCU 150. More particularly, DISENGAGE key may correspond to switch 312 of wireless RCU 148 and/or switch 312' of wired RCU 150. If it is determined in step 1022 that the DISENGAGE key is pressed, a disengage operation is performed in step 1024. After the execution of step 1024, control is transferred to loop 1034.

If it is determined in step 1022 that DISENGAGE key is not pressed, an IDLE routine is performed in step 1026.

In step 1028, it is determined whether to end the operation of the main operating program. If it is determined in step 1028 to not end the operation of the main operating program, control is transferred to loop 1034. If, however, it is determined in step 1028 to end or terminate the operation of the main operating program, a shutdown routine is executed in step 1030, and the main operating program is thereafter terminated in step 1032.

It should be appreciated that the main operating program may determine which, if any, key is pressed in the order illustrated in FIG. 13 or in any other appropriate order. It should also be appreciated that the main operating program illustrated in FIG. 13, as well as the routines illustrated in FIGS. 14a-14d, 15a, 15b and 16, may be embodied, for example, in a messaging-based, event-driven and/or polling-type software application.

Referring now to FIGS. 14a-14d, there is seen a flowchart of a firing routine specific to a circular surgical stapler attachment 250, such as that illustrated in FIG. 9. It should be appreciated that the firing routine illustrated in FIGS. 14a-14d represents the routine A of step 1008 of the main operating program illustrated in FIG. 13 and that the firing routine illustrated in FIGS. 14a-14d is specific to a circular surgical stapler attachment 250, such as that illustrated in FIG. 9. It should be further appreciated that other surgical instruments or attachments, such as those enumerated above, may have other firing routines associated therewith.

Proceeding from step 1008, it is determined in step 1100 whether the DLU—the circular surgical stapler attachment 250 has been fully opened. This determination may be made based on the signals generated by the encoders 106, 108, as more fully described above. If it is determined in step 1100 that the DLU has not been fully opened, an ERROR condition is determined in step 1102 in that the DLU is not ready for firing. Control is then transferred to step 1120, wherein control returns to the main operating program illustrated in FIG. 13.

If it is determined in step 1100 that the DLU has been fully opened, it is determined in step 1104 whether the DLU has been fully clamped. This determination may be made based on the signals generated by the encoders 106, 108, as more fully described above. If it is determined in step 1104 that the DLU has not been fully clamped, an ERROR condition is determined in step 1106 in that the DLU is not within an acceptable range for firing. Control is then transferred to step 1120, wherein control returns to the main operating program illustrated in FIG. 13.

If it is determined in step 1104 that the DLU has been fully clamped, it is determined in step 1108 whether the DLU has been previously fired. This determination may be made based on the signals generated by the encoders 106, 108 and/or in accordance with usage data 184. If it is determined in step 1108 that the DLU has been previously fired, an ERROR condition is determined in step 1110 in that the DLU has been used. Control is then transferred to step 1120, wherein control returns to the main operating program illustrated in FIG. 13. It should be appreciated that a similar usage determination may be made in the main operating program illustrated in FIG. 13, for example, in the initialization step 1002 or in the DLU presence determining step 1004, as an alternative or in addition to the determining step 1108.

If it is determined in step 1108 that the DLU has not been previously fired, a usage count is decremented in step 1112. The usage count may be stored in usage data 184 as more fully described hereinabove. Several attempts at decrementing the usage count may be made in step 1112. However, a failure to decrement the usage count may nevertheless occur. In step 1114, it is determined whether the usage count decrementing step 1112 has failed. If it is determined in step 1114 that the decrementing of usage count failed, a ERROR condition is determined in step 1116. Thereafter, in step 1118, a wait loop is executed until all keys of the wireless RCU 148 and/or wired RCU 150 have been released. After it is determined in step 1118 that all keys have been released, control is transferred to step 1120. Thereafter, control returns to the main operating program illustrated in FIG. 13.

If it is determined in step 1114 that the usage count decrementing did not fail, the firing motor current limit is set in step 1122. In this context, the firing motor may correspond to the second motor 80 as more fully described hereinabove. The firing motor is then started in step 1124 to begin the advancement of the staple driver/cutter 264.

Figure 14A:
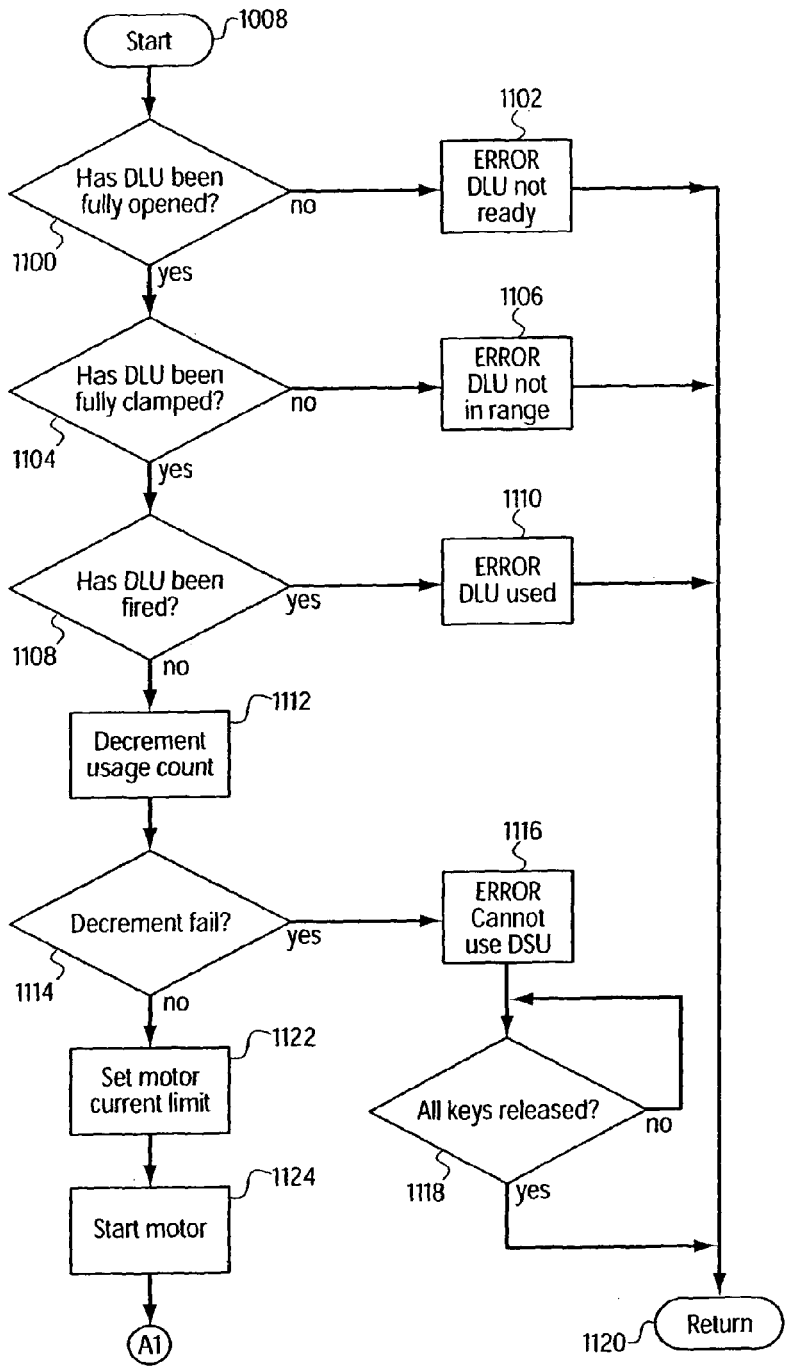
FIGS. 14a-14d illustrate a flowchart of a fire routine for a circular surgical stapler attachment, such as that illustrated in FIG. 9.
Figure 14B:
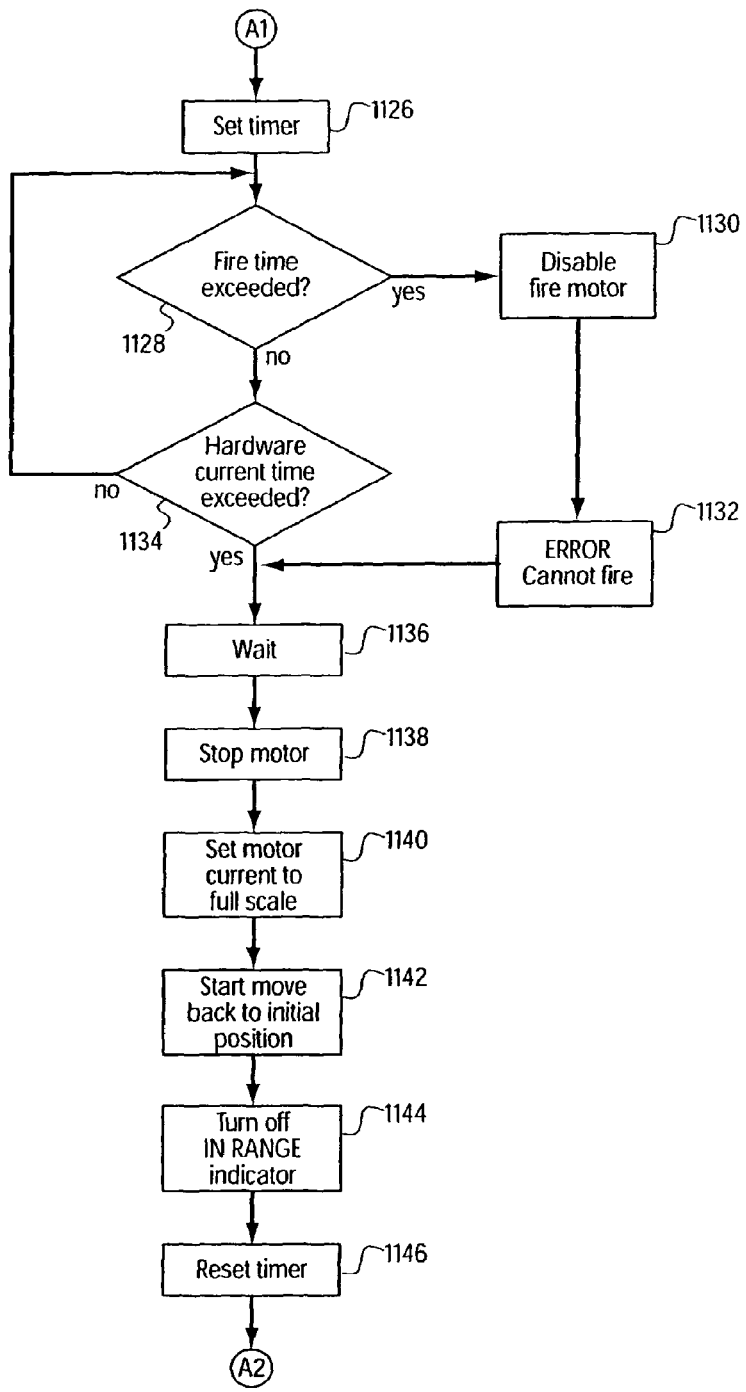

Referring now to FIG. 14*b*, a timer is set in step 1126. It is thereafter determined in step 1128 whether the time elapsed for the firing operation has exceeded a predetermined threshold. If it is determined in step 1128 that the firing time limit has been exceeded, the firing motor is disabled in step 1130, and an ERROR condition is determined in step 1132. Control then proceeds to step 1136. If, however, it is determined in step 1128 that the firing time has not exceeded the predetermined firing time limit, it is determined in step 1134 whether a hardware current limit has been exceeded. The hardware current limit relates to the resistance of the firing motor to continued operation. A condition that the hardware current limit has been exceeded is indicative that the stapling operation has been successfully completed. If it is determined in step 1134 that the hardware current limit has not been exceeded, the operation of firing motor is continued until either the predetermined firing time limit has been exceeded or the hardware current limit has been exceeded. In either instance control proceeds thereafter to step 1136.

Step 1136 represents a waiting step, during which a predetermined wait time is permitted to elapse. This wait time permits the driving and driven elements of electromechanical surgical device 10 and circular surgical stapler attachment 250 to come to rest before proceeding to step 1138, in which step the firing motor is stopped.

After the firing motor is stopped in step 1138, the motor current limit is set to full scale in step 1140, and then the firing motor is started in step 1142 in a reverse direction to retract the staple driver/cutter 264 and return the same to its initial position. Then, once the gap between the anvil 256 and the body portion 252 has exceeded the acceptable range, the indicator 18*a*, 18*b* corresponding to an IN-RANGE indicator is turned off in step 1144. Alternatively, the IN-RANGE indicator may be turned off in step 1144 upon the start of the reversal of the motor in step 1142. After the IN-RANGE indicator is turned off in step 1144, the timer is reset in step 1146.

Figure 14C:
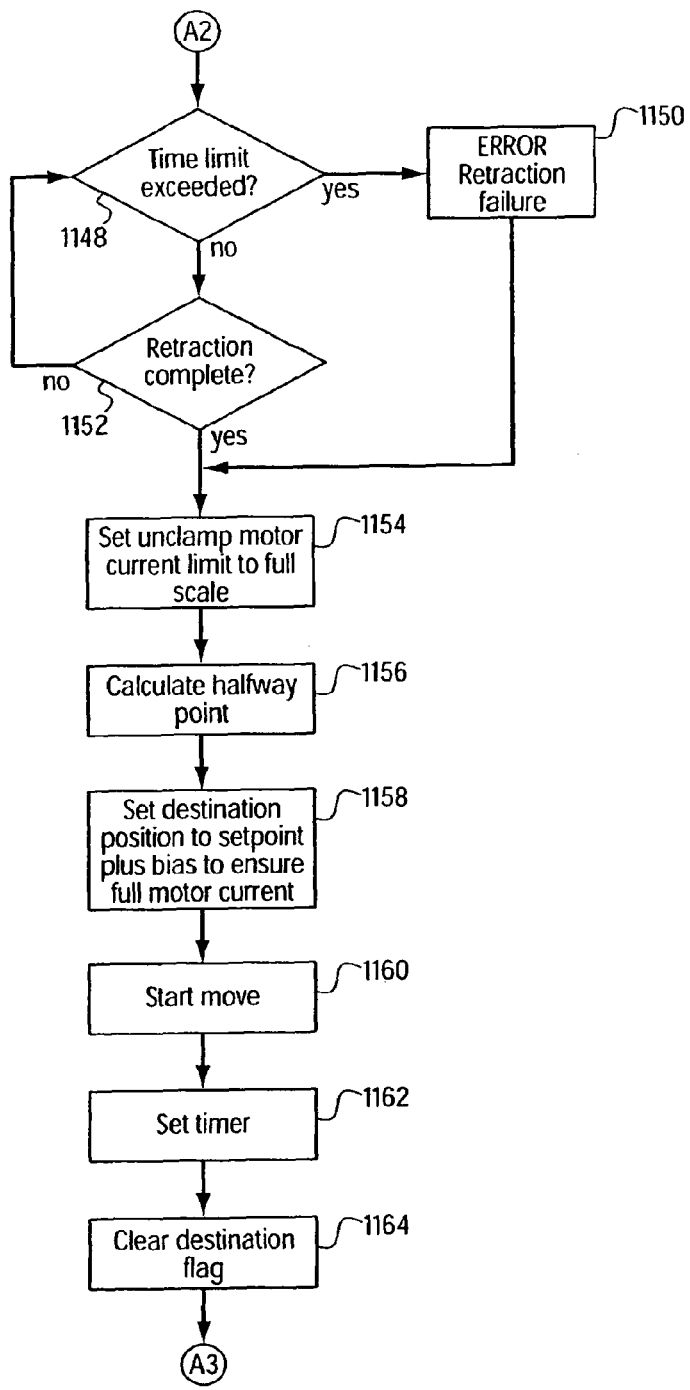

Referring now to FIG. 14*c*, it is determined in step 1148 whether a predetermined time limit for completing the retraction of the staple driver/cutter 264, based on the timer reset in step 1146, has been exceeded. If it is determined in step 1148 that the predetermined time limit has been exceeded, an ERROR condition is determined in step 1150 in that the retraction operation failed to be completed within the permissible predetermined time limit. If, however, it is determined in step 1148 that the predetermined time limit has not been exceeded, it is determined in step 1152 whether retraction of the staple driver/cutter 264 has been completed. If it is determined in step 1152 that the retraction of the staple driver/cutter 264 has not been completed, control returns to step 1148. Retraction of staple driver/cutter 264 continues until either the predetermined time limit has been exceeded as determined in step 1148 or the retraction has been completed as determined in step 1152. It should be appreciated that the determination made in step 1152 may be based on the signals generated by the encoders 106, 108. After it is determined that the retraction of staple driver/cutter 264 has been completed (step 1152) or that the predetermined time limit has been exceeded (step 1148), the unclamp motor current limit is set of full scale in step 1154. In this context, the unclamp motor may correspond to first motor 76 as more fully described hereinabove.

In step 1156, the halfway point between the current position of the anvil 256 and the final, unclamped position of the anvil 256 is calculated. A "phantom" destination position is set in step 1158 to a predetermined setpoint plus a predetermined bias value to ensure that the unclamp motor achieves its maximum, or full, current to thereby ensure the maximum torque output from the unclamp motor. In step 1160, the movement of the unclamp motor is initiated. In step 1162, the timer is set, and in step 1164 a destination flag is cleared.

Figure 14D:
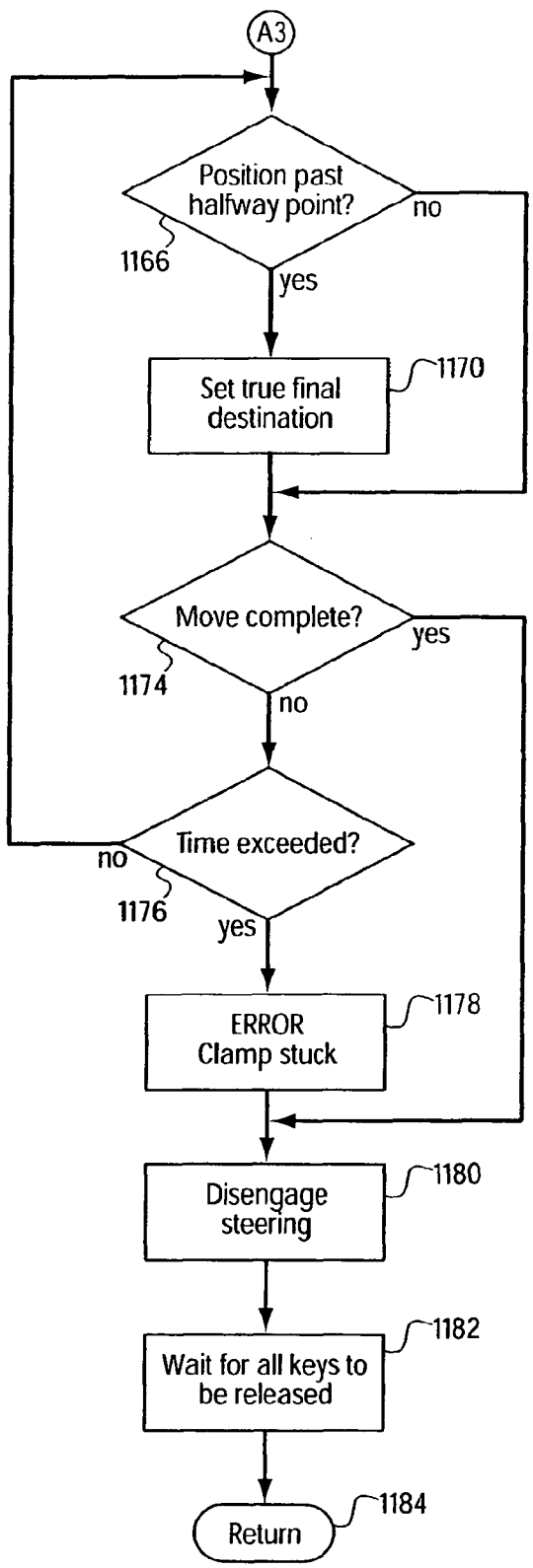

Referring now to FIG. 14*d*, it is determined in step 1166 whether the anvil 256 has passed the halfway point determined in step 1156. If it is determined in step 1166 that the anvil 256 has passed the halfway point determined in step 1156, the "true" final destination position for the anvil 256 is set in step 1170, thereby superceding the "phantom" final destination set in step 1158. Control is then transferred to step 1174. If, however, it is determined in step 1166 that the position of the anvil 256 is not past the halfway point determined in step 1156, control is directly transferred to step 1174, bypassing the destination resetting step 1170.

In step 1174, it is determined whether the anvil 256 has reached the "true" final destination set in step 1170. It should be appreciated that the position of the anvil 256 may be determined in accordance with the signals output by encoders 106, 108 as more fully described hereinabove. If it is determined in step 1174 that anvil 256 has reached its "true" final destination set in step 1170, control is transferred to step 1180, described below. If, however, it is determined in step 1174 that the "true" final destination of the anvil 256 has not been reached, it is determined in step 1176, with reference to the timer reset in step 1162, whether a predetermined time limit has been exceeded. If it is determined in step 1176 that the predetermined time limit has not been exceeded, control is returned to step 1166, and the unclamp motor continues its operation to further unclamp the anvil 256. If, however, it is determined in step 1176 that the predetermined time limit has been exceeded, and ERROR condition is determined in step 1178 in that the anvil 256 could be moved into its "true" final destination within the predetermined time limit. Control is thereafter transferred to step 1180, in which the steering mechanism is disengaged. In the example embodiment of electromechanical surgical device 10 described above, the steering mechanism may include the fifth motor 96 and/or carriage 100 as more fully described hereinabove. After the steering mechanism has been disengaged in step 1180, a wait loop is executed in step 1182 until all keys of wireless RCU 148 and/or wired RCU 150 have been released. Once all of the keys have been released, control returns in step 1184 to the main operating program illustrated in FIG. 13.

Figure 15A:
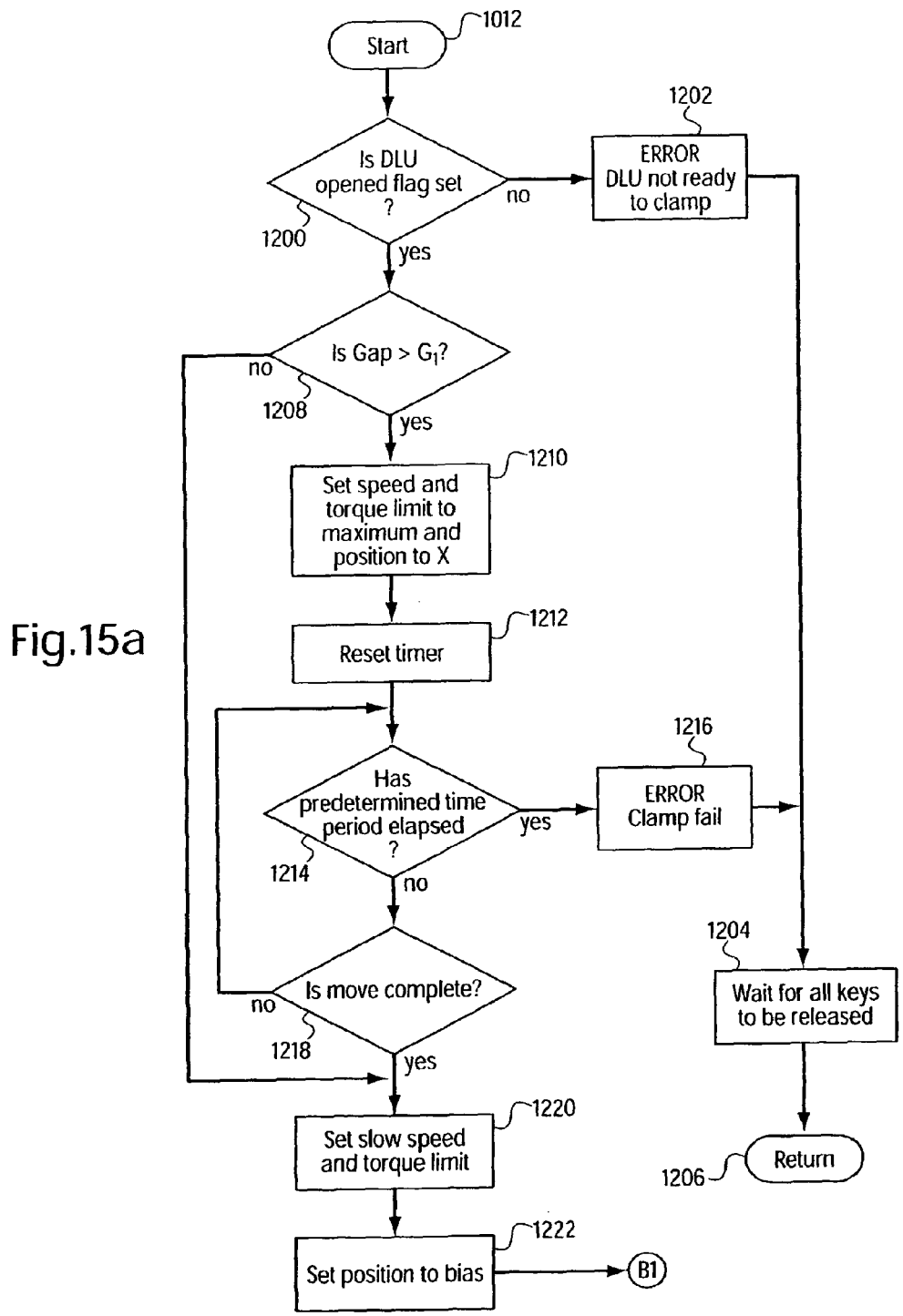
FIGS. 15a and 15b illustrate a flowchart of a clamp routine for a circular surgical stapler attachment, such as that illustrated in FIG. 9.
Figure 15B:
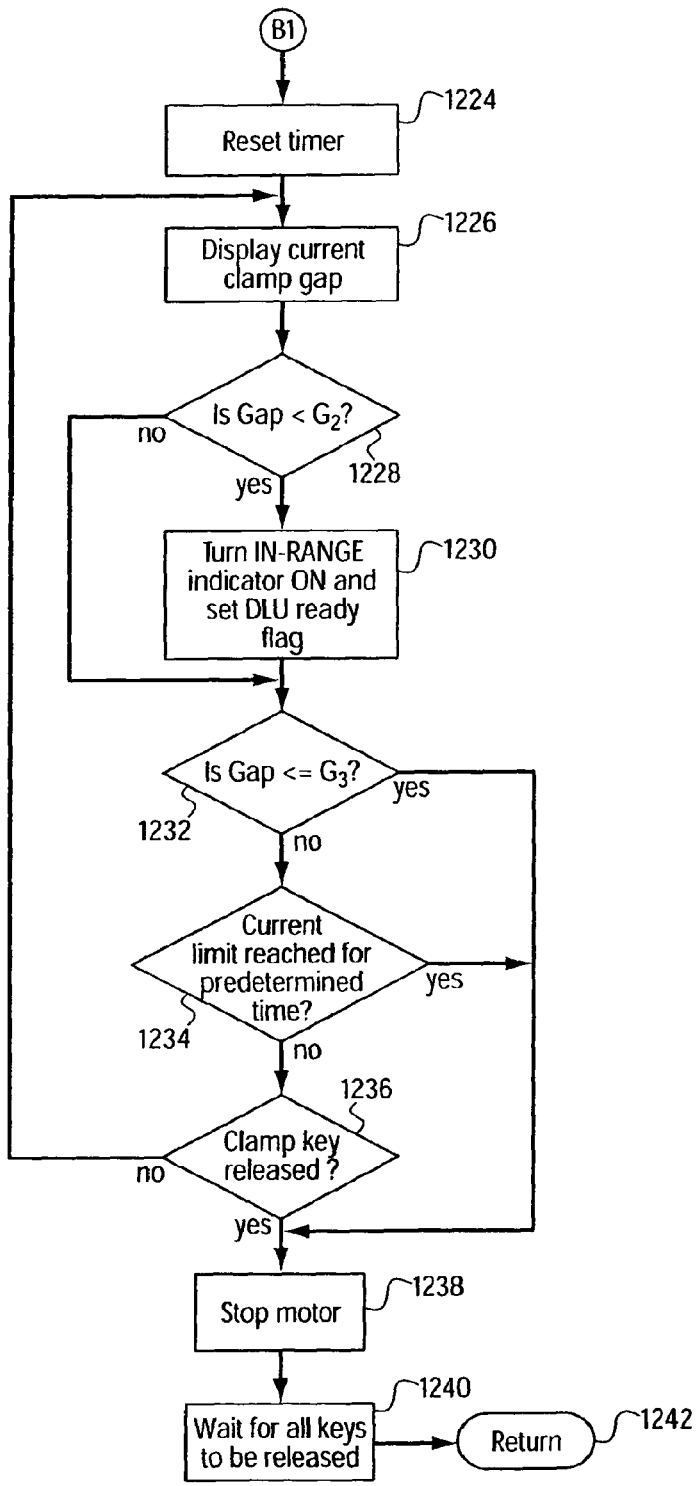

Referring now to FIGS. 15a and 15b, there is seen a flowchart of a clamp routine specific to a circular surgical stapler attachment 250, such as that illustrated in FIG. 9. It should be appreciated that the clamp routine illustrated in FIGS. 15a and 15b represents the routine B of step 1012 of the main operating program illustrated in FIG. 13 and that the clamp routine illustrated in FIGS. 15a and 15b is specific to a circular surgical stapler attachment 250, such as that illustrated in FIG. 9. It should be further appreciated that other surgical instruments or attachments, such as those enumerated above, may have other clamping routines associated therewith.

Proceeding from step 1012, it is determined in step 1200 whether a DLU open flag is set. If it is determined in step 1200 that the DLU open flag is not set, an ERROR condition is determined in step 1202 in that the DLU is not ready to clamp. A wait loop is executed thereafter in step 1204, and once all keys of wireless RCU 148 and/or wired RCU 150 have been released, control returns in step 1206 to the main operating program illustrated in FIG. 13.

If, however, it is determined in step 1200 that the DLU open flag is set, it is determined in step 1208 whether the gap between the anvil 256 and the body portion 252 is greater than a predetermined threshold $G_1$, such as, for example, 5.0 mm. This determination may be made based on the signals generated by the encoders 106, 108, as more fully described above. If it determined that the gap between the anvil 256 and the body portion 252 is less than the predetermined threshold $G_1$, control proceeds to step 1220. If, however, it is determined in step 1208 that the gap between the anvil 256 and the body portion 252 is greater than the predetermined threshold $G_1$, control proceeds to step 1210 in which a CLAMP motor speed and torque limit are set to the respective maximum values. In this context, the CLAMP motor may correspond to first motor 76 as more fully described hereinabove. A timer is reset in step 1212, and the control loop of steps 1214 and 1218 is executed until either a predetermined time period for reaching a gap of less than the predetermined threshold $G_1$ is exceeded or the gap is determined to be less than the predetermined threshold $G_1$. If it is determined in step 1214 that the predetermined time period has been exceeded, an ERROR condition is determined in step 1216 in that the clamp operation is considered to have failed. After step 1216 is performed, step 1204 is performed, in which a wait loop is executed until all keys of wireless RCU 148 and/or wired RCU 150 have been released. Thereafter, control returns in step 1206 to the main operating program illustrated in FIG. 13.

If it is determined in step 1214 that the predetermined time period has not been exceeded, it is determined in step 1218 whether the movement of the anvil 256 to a location in which the gap between the anvil 256 and the body portion 252 is less than the predetermined threshold $G_1$ has been completed. If it is determined in step 1218 that this move has not been completed, the operation of CLAMP motor is continued, and control returns to step 1214. If however, it is determined in step 1218 that the move is complete, control proceeds to step 1220.

In step 1220, a speed lower than the maximum speed set in step 1210 is set for the CLAMP motor and a torque limit lower than the torque limit set in step 1210 is set for the CLAMP motor. Thereafter, in step 1222, a position bias is set to ensure that the CLAMP motor outputs full torque when the gap between the anvil 256 and the body portion 252 approaches the bias value. The bias value may be, for example, approximately 1.0 mm to ensure full torque output from the CLAMP motor when the gap is approximately equal to 1.0 mm.

Referring now to FIG. 15b, control proceeds to step 1224, in which a timer is reset. In step 1226, the value of the current gap between the anvil 256 and the body portion 252 is displayed on the display device 16. In step 1228, it is determined whether the gap between the anvil 256 and the body portion 252 is less than a predetermined threshold $G_2$. This determination may be made based on the signals generated by the encoders 106, 108, as more fully described above. The predetermined threshold $G_2$ may be, for example, 2.0 mm. If the gap between the anvil 256 and the body portion 252 is determined in step 1228 to be less than the predetermined threshold $G_2$, control proceeds to step 1230, in which an IN-RANGE indicator is activated and a DLU ready flag is set. The IN-RANGE indicator may correspond to one of the indicators 18a, 18b, either one or both of which may be, for example, LED elements or other audio or visual indicators. If it is determined in step 1228 that the gap between the anvil 256 and the body portion 252 is not less than the predetermined threshold $G_2$, control proceeds to step 1232, in which it is determined whether the gap between the anvil 256 and the body portion is less than or equal to another predetermined threshold $G_3$. This determination may be made based on the signals generated by the encoders 106, 108, as more fully described above. The predetermined threshold $G_3$ may be, for example, 1.0 mm. If it is determined in step 1232 that the gap between the anvil 256 and the body portion 252 is less than or equal to the predetermined threshold $G_3$, control proceeds to step 1238, described below. However, if it is determined in step 1232 that the gap between the anvil 256 and the body portion 252 is greater than the predetermined threshold $G_3$, it is determined in step 1234 whether the current limit to the CLAMP motor has been reached for a predetermined time limit. That the current limit to the CLAMP motor has been reached for the predetermined time limit is indicative that tissue is fully clamped between the anvil 256 and the body portion 252. The predetermined time limit may be, for example, 1.0 second. If it is determined in step 1234 that the current limit to the CLAMP motor has been reached for the predetermined time limit, control proceeds to step 1238. If, however, it is determined in step 1234 that the current limit to the CLAMP motor has not been exceeded for the predetermined time limit, it is determined in step 1236 whether the CLAMP key has been released. If it is determined in step 1236 that the CLAMP key has not been released, control returns to step 1226. If it is determined in step 1236 that the CLAMP key has been released, control proceeds to step 1238.

In step 1238, the operation of the CLAMP motor is stopped. Thereafter, in step 1240, a wait loop is executed until all keys of wireless RCU 148 and/or wired RCU 150 have been released. After all keys have been released, control returns in step 1242 to the main operating program illustrated in FIG. 13.

Figure 16:
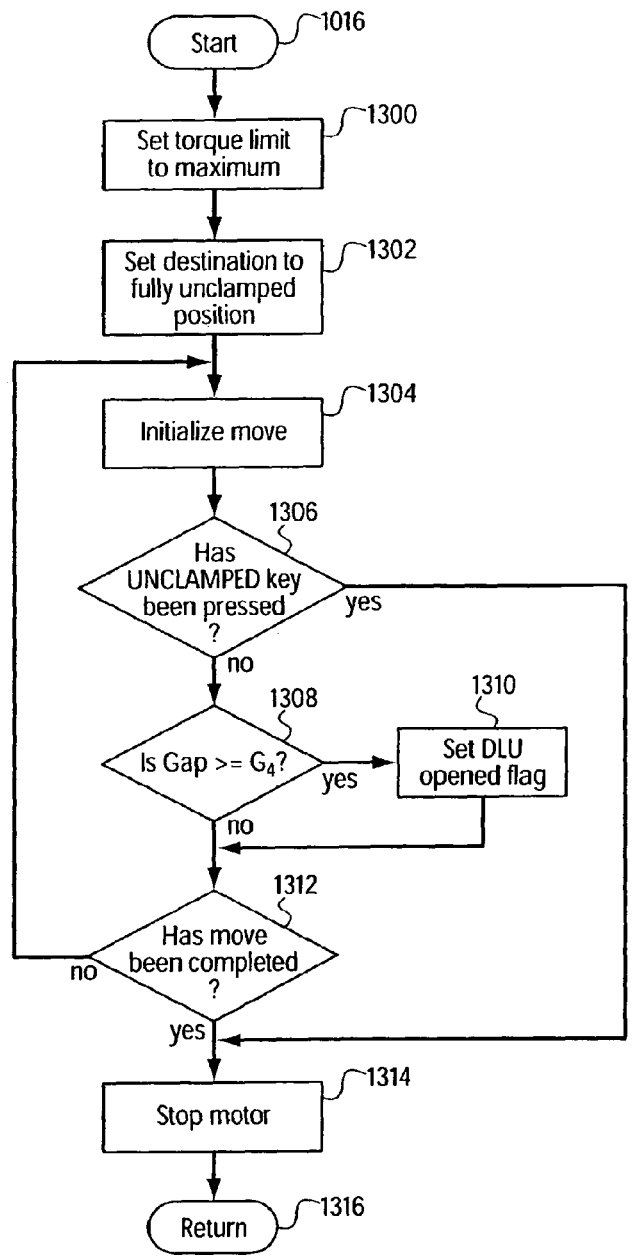
FIG. 16 illustrates a flowchart of an unclamp routine for a circular surgical stapler attachment, such as that illustrated in FIG. 9.

Referring now to FIG. 16, there is seen a flowchart of an unclamp routine specific to a circular surgical stapler attachment 250, such as that illustrated in FIG. 9. It should be appreciated that the unclamp routine illustrated in FIG. 16 represents the routine C of step 1016 of the main operating program illustrated in FIG. 13 and that the unclamp routine illustrated in FIG. 16 is specific to a circular surgical stapler attachment 250, such as that illustrated in FIG. 9. It should be further appreciated that other surgical instruments or attachments, such as those enumerated above, may have other unclamp routines associated therewith.

Proceeding from step 1016, a torque limit for an UNCLAMP motor is set in step 1300 to its maximum value. The UNCLAMP motor may correspond to the CLAMP motor as more fully described hereinabove. The UNCLAMP motor may also correspond to the first motor 76 as more fully described hereinabove.

In step 1302, the destination position for the anvil 256 is set to a value representative of its fully unclamped position. The operation of the UNCLAMP motor is initiated in step 1304. In step 1306, it is determined whether the UNCLAMP key has been released. If it is determined in step 1306 that the UNCLAMP key has been released, control proceeds to step 1314. If it is determined in step 1306 that the UNCLAMP key has not been released, it is determined in step 1308 whether the gap between the anvil 256 and the body portion 252 is greater than or equal to a predetermined threshold $G_4$, which is defined in accordance with the destination position set in step 1302. This determination may be made based on the signals generated by the encoders 106, 108, as more fully described above. If it is determined in step 1308 that the gap between the anvil 256 and the body portion 252 is greater than or equal to the predetermined threshold $G_4$, a DLU opened flag is set in step 1310. Control then proceeds to step 1312. If it is determined in step 1308 that the gap between the anvil 256 and the body portion 252 is less than the predetermined threshold $G_4$, it is determined in step 1312 whether the unclamp operation is complete. That is, whether the destination position for the anvil 256 set in step 1302 has been reached. If it is determined in step 1312 that the movement of the anvil 256 is not complete, control returns to step 1306. If it is determined in step 1312 that the movement of the anvil 256 is complete, the operation of the UNCLAMP motor is stopped in step 1314. Control then returns in step 1316 to the main operating program illustrated in FIG. 13.

It should be understood that the operation of the several motors and switch elements as described above with respect to the circular surgical stapler attachment 250 are specific to the circular surgical stapler attachment 250. The motor(s) and/or switch(es) may perform other functions when other surgical instruments or attachments are attached to flexible shaft 20.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby and that its scope is to be determined by that of the appended claims.

The invention claimed is:

1. An electro-mechanical surgical device, comprising:
a housing;
an elongated shaft extending from the housing;
a controller provided in the housing, the controller configured to control operations of the electro-mechanical surgical device;
a first, second, third, and fourth steering cable, each cable extending through the shaft and configured to mechanically cooperate with a surgical instrument attachable to a distal end of the shaft;
a plurality of motors connected to the controller, where the plurality of motors are attached to a proximal portion of at least one of the first, second, third, and fourth steering cables;
a wired remote control unit (RCU) electrically and logically connected to the controller; and
a wireless remote control unit (RCU) configured to communicate with a transceiver electrically and logically connected to the controller,
wherein the wired RCU and the wireless RCU each include:
a first set of switches arranged under a four-way rocker for controlling the first and second steering cables via one motor of the plurality of motors, and the third and fourth steering cables via another motor of the plurality of motors;
a second set of switches arranged under a two-way rocker for controlling one or more functions of the surgical instrument attached to the distal end of the elongated shaft; and
a third switch, separate and distinct from the first and second set of switches, the third switch configured to transmit at least one data signal to the transceiver, the at least one data signal including identification data to prevent unauthorized operation of the electro-mechanical surgical device.

2. The electro-mechanical surgical device according to claim 1, wherein a memory unit is electrically and logically connected to the controller.

3. The electro-mechanical surgical device according to claim 2, wherein the controller is configured to read and select from the memory unit an operating program or algorithm corresponding to a type of surgical instrument attached to the elongated shaft.

4. The electro-mechanical surgical device according to claim 3, wherein, once the controller reads and selects the operating program or algorithm, the controller causes the operating program or algorithm to be executed in accordance with operations performed by the wired RCU or the wireless RCU.

5. The electro-mechanical surgical device according to claim 1, wherein the wireless RCU includes a steering engage/disengage switch for selectively engaging/disengaging a steering mechanism operably coupled to at least one motor of the plurality of motors.

6. The electro-mechanical surgical device according to claim 1, wherein the plurality of motors includes at least a first motor and a second motor, the first and second motors operably coupled to a first encoder and a second encoder, respectively, the first and second encoders positioned within a coupling adapted to detachably secure the surgical instrument to the elongated shaft.

7. The electro-mechanical surgical device according to claim 1, wherein the elongated shaft includes at least two rotatable drive shafts disposed therein, each of the rotatable drive shafts configured to include a magnet mounted thereon for producing a magnetic field in operable communication with at least one encoder including at least two sensors disposed approximately 90° apart relative to a longitudinal axis of each of the rotatable drive shafts.

8. The electro-mechanical surgical device according to claim 7, wherein an output of the at least two sensors is adapted to be adjusted as a function of a change of polarity of the magnetic field in a detection range of the at least two sensors.

9. An electro-mechanical surgical device, comprising:
a housing;
an elongated shaft extending from the housing;
a controller provided in the housing;
a steering arrangement extending through the elongated shaft and mechanically cooperating with a surgical instrument attachable to a distal end of the shaft;
a plurality of motors connected to the controller, at least one of the plurality of motors configured to drive the steering arrangement;
a wired remote control unit (RCU) electrically and logically connected to the controller; and
a wireless remote control unit (RCU) configured to communicate with a transceiver electrically and logically connected to the controller,
wherein the wired RCU and the wireless RCU each include:
a first set of switches arranged under a four-way rocker for controlling first and second steering cables of the steering arrangement via one motor of the plurality of motors, and third and fourth steering cables of the steering arrangement via another motor of the plurality of motors;
a second set of switches arranged under a two-way rocker for controlling one or more functions of the surgical instrument attached to the distal end of the elongated shaft; and
a third switch, separate and distinct from the first and second set of switches, the third switch configured to transmit at least one data signal to the transceiver, the at least one data signal including identification data to prevent unauthorized operation of the surgical device.

10. The electro-mechanical surgical device according to claim 9, wherein a memory unit is electrically and logically connected to the controller.

11. The electro-mechanical surgical device according to claim 10, wherein the controller is configured to read and select from the memory unit an operating program or algorithm corresponding to a type of surgical instrument attached to the elongated shaft.

12. The electro-mechanical surgical device according to claim 11, wherein, once the controller reads and selects the operating program or algorithm, the controller causes the operating program or algorithm to be executed in accordance with operations performed by the wired RCU or the wireless RCU.

13. The electro-mechanical surgical device according to claim 9, wherein the wireless RCU includes a steering engage/disengage switch for selectively engaging/disengaging the steering arrangement operably coupled to the at least one motor of the plurality of motors.

14. The electro-mechanical surgical device according to claim 9, wherein the plurality of motors includes a first motor and a second motor, the first and second motors operably coupled to a first encoder and a second encoder, respectively, the first and second encoders positioned within a coupling adapted to detachably secure the surgical instrument to the elongated shaft.

15. The electro-mechanical surgical device according to claim 9, wherein the elongated shaft includes at least two rotatable drive shafts disposed therein, each of the rotatable drive shafts configured to include a magnet mounted thereon for producing a magnetic field in operable communication with at least one encoder including at least two sensors disposed approximately 90° apart relative to a longitudinal axis of each of the rotatable drive shafts.

16. The electro-mechanical surgical device according to claim 15, wherein an output of the at least two sensors is adapted to be adjusted as a function of a change of polarity of the magnetic field in a detection range of the at least two sensors.

\* \* \* \* \*